(12) United States Patent
Takahashi

(10) Patent No.: US 8,139,711 B2
(45) Date of Patent: Mar. 20, 2012

(54) RADIATION PHASE IMAGE RADIOGRAPHING APPARATUS

(75) Inventor: Kenji Takahashi, Kanagawa-ken (JP)

(73) Assignee: Fujifilm Corporation, Tokyo (JP)

( * ) Notice: Subject to any disclaimer, the term of this patent is extended or adjusted under 35 U.S.C. 154(b) by 224 days.

(21) Appl. No.: 12/585,283

(22) Filed: Sep. 10, 2009

(65) Prior Publication Data

US 2010/0061508 A1    Mar. 11, 2010

(30) Foreign Application Priority Data

Sep. 11, 2008  (JP) ................................. 2008-232867

(51) Int. Cl.
*G03H 5/00*    (2006.01)
*G01N 23/20*   (2006.01)
*G01B 9/021*   (2006.01)

(52) U.S. Cl. .............................. 378/36; 378/71; 356/457

(58) Field of Classification Search .................... 378/36, 378/70, 71, 156–7, 145, 204, 210; 356/300, 356/302, 305, 328, 28.5, 35.5, 450, 451, 356/453–457, 477, 491–494, 498–500, 521, 356/900, 902, 903; 385/10

See application file for complete search history.

(56) References Cited

U.S. PATENT DOCUMENTS

| 5,812,629 | A | 9/1998 | Clauser |
| 7,180,979 | B2 | 2/2007 | Momose |
| 2007/0183563 | A1* | 8/2007 | Baumann et al. ............... 378/19 |
| 2009/0092227 | A1* | 4/2009 | David et al. .................... 378/36 |

FOREIGN PATENT DOCUMENTS

JP    2006-259264    9/2006

\* cited by examiner

*Primary Examiner* — Anastasia Midkiff
(74) *Attorney, Agent, or Firm* — Jean C. Edwards, Esq.; Edwards Neils PLLC

(57) ABSTRACT

A radiation phase image radiographing apparatus, including a radiation emission unit having multiple radiation sources for emitting radiation onto a subject, the radiation sources being distributed such that radiation emitted from each of the radiation sources and transmitted through the subject forms a part of a projected image of the subject, a first diffraction grating configured to be exposed to the radiation emitted from the multiple radiation sources of the radiation emission unit and to produce a Talbot effect by the exposure, a second diffraction grating for diffracting the radiation diffracted by the first diffraction grating, and a radiation image detector for detecting the radiation diffracted by the second diffraction grating.

25 Claims, 23 Drawing Sheets

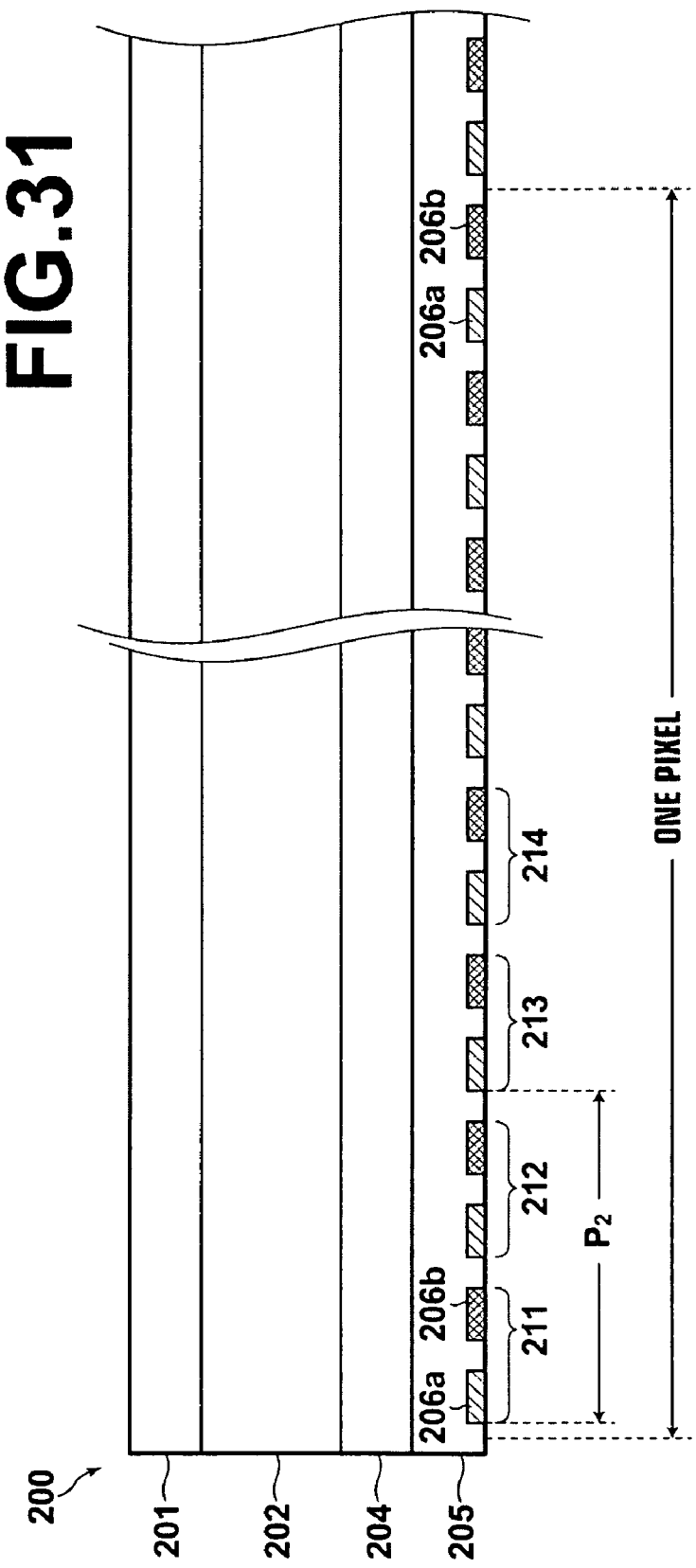

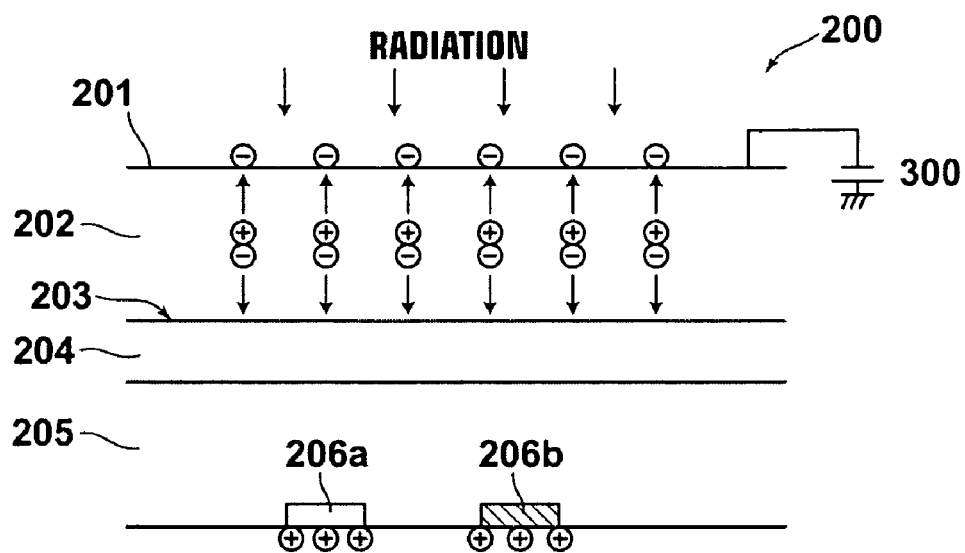
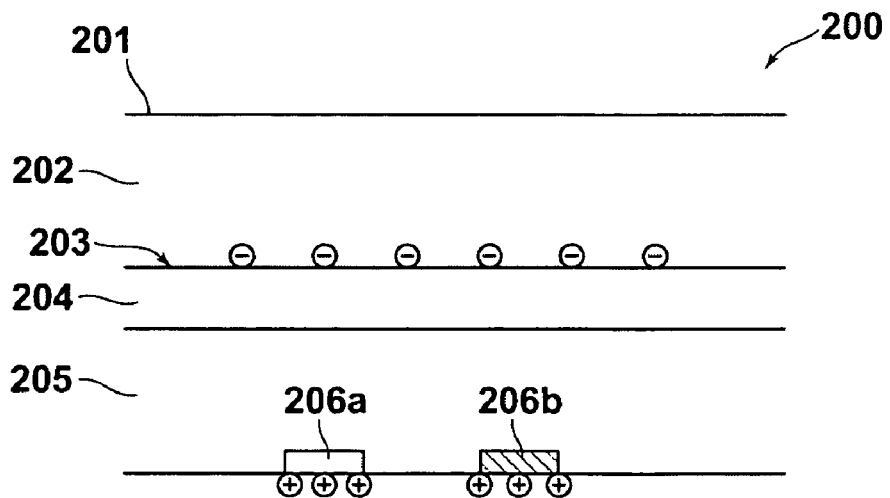

RADIATION PHASE IMAGE RADIOGRAPHING APPARATUS

CROSS-REFERENCE TO RELATED APPLICATIONS

The present application claims priority from Japanese Patent Application No. 2008-232867, filed Sep. 11, 2008, the contents of which are herein incorporated by reference in their entirety.

BACKGROUND OF THE INVENTION

1. Field of the Invention

The present invention relates to a radiation phase image radiographing apparatus using a Talbot interferometer.

2. Description of the Related Art

The use of a Talbot interferometer, which produces Talbot effect by a diffraction grating and generates Moire fringes in combination with another diffraction grating, to X-ray applications has been studied as described, for example, in U.S. Pat. No. 5,812,629 (Patent Document 1) and U.S. Pat. No. 7,180,979 (Patent Document 2).

For example, Patent Document 2 proposes an X-ray imaging apparatus using a Talbot interferometer that includes an X-ray source, two diffraction gratings, and an X-ray image detector.

In the X-ray imaging apparatus described in Patent Document 2, both the two diffraction gratings and X-ray image detector are formed on a planar substrate. Where parallel beam, such as synchrotron radiation is used, the planar shape described above does not pose any problems, but it gives rise to a problem in medical diagnostic applications and the like in which an X-ray source that radiates widely spreading beams is generally used. That is, X-rays pass through the diffraction gratings at a center portion without any difficulty, but at a portion other than the center portion, X-rays are blocked by diffraction members and unable to pass through the diffraction gratings because the X-rays are incident from oblique directions. For example, Japanese Unexamined Patent Publication No. 2006-259264 (Patent Document 3) proposes an amplitude diffraction grating in which metal X-ray absorption members, each having a width of 2 to 10 µm and a thickness of 25 to 100 µm, are disposed at an equal interval of 2 to 10 µm. It can be thought that the use of such a diffraction grating may possibly cause the problem described above. Accordingly, large-size X-ray phase imaging has been difficult in medical diagnostic applications.

In view of the circumstances described above, it is an object of the present invention to provide a radiation phase image radiographing apparatus capable of performing large-size radiation phase imaging.

SUMMARY OF THE INVENTION

A first radiation phase image radiographing apparatus of the present invention is an apparatus, including:

a radiation emission unit having multiple radiation sources for emitting radiation onto a subject, the radiation sources being distributed such that radiation emitted from each of the radiation sources and transmitted through the subject forms a part of a projected image of the subject;

a first diffraction grating configured to be exposed to the radiation emitted from the multiple radiation sources of the radiation emission unit and to produce a Talbot effect by the exposure;

a second diffraction grating for diffracting the radiation diffracted by the first diffraction grating; and a radiation image detector for detecting the radiation diffracted by the second diffraction grating.

In the first radiation phase image radiographing apparatus of the present invention, the multiple radiation sources may be disposed along a planar surface, and the first and second diffraction gratings may be formed respectively along planar surfaces parallel to the planar surface on which the multiple radiation sources are disposed.

Further, the multiple radiation sources may be disposed along a cylindrical surface, and the first and second diffraction gratings may be formed respectively along cylindrical surfaces concentric with the cylindrical surface on which the multiple radiation sources are disposed.

Still further, the multiple radiation sources or the radiation image detector may be disposed in abutment with a cylindrical surface centered on a position where the subject is placed, and the first and second diffraction gratings may be formed respectively in abutment with cylindrical surfaces concentric with the cylindrical surface to which the multiple radiation sources or the radiation image detector is abutted.

Further, each of the multiple radiation sources may be a radiation source that emits radiation such that exposure areas of adjacent radiation sources at a position of the subject overlap with each other without any space between them and at an angle that substantially does not influence diffraction properties of the first and second diffraction gratings in peripheral portions of exposure areas at the positions of the first and second diffraction gratings.

Still further, a spread angle of the radiation emitted from each of the multiple radiation sources in an extending direction of a diffraction member of the first diffraction grating may be made larger than a spread angle of the radiation in a direction orthogonal to the extending direction.

Further, an arrangement area of the multiple radiation sources in an extending direction of a diffraction member of the first diffraction grating may be made smaller than an arrangement area of the radiation sources in a direction orthogonal to the extending direction.

Still further, all of the multiple radiation sources may be disposed in a line in a direction orthogonal to the extending direction of the diffraction member of the first diffraction grating.

Further, each of the radiation sources may be a micro-focus X-ray source, and a Talbot interferometer may be constructed with the first and second diffraction gratings.

Still further, each of the radiation sources may be an X-ray source constituted by an electron source, a metal target, and a slit made of linear members parallel to diffraction members of the first and second diffraction gratings and transmits an X-ray emitted from the metal target, and a Talbot interferometer may be constructed with the first and second diffraction gratings.

Further, a shifting mechanism for shifting the first and second diffraction gratings in a direction orthogonal to an extending direction of diffraction members of the first and second diffraction gratings may be provided, and a phase image may be formed based on image signals detected by the radiation image detector at a plurality of positions according to the shift of the first and second diffraction gratings implemented by the shifting mechanism.

Still further, a partial phase image may be generated with respect to each detection area of the radiation image detector corresponding to an exposure area of the radiation emitted from each radiation source based on image signals corresponding to a plurality of phase components, each detected by each detection area, and a complete phase image is formed by combining the partial phase images.

Further, among image signals detected by the radiation image detector, only a signal detected by a detection area of the radiation image detector corresponding to an exposure area of the radiation emitted from each radiation source and propagated straightly may be extracted.

A second radiation phase image radiographing apparatus of the present invention is an apparatus, including:

a radiation emission unit having multiple radiation sources for emitting radiation onto a subject, the radiation sources being distributed such that radiation emitted from each of the radiation sources and transmitted through the subject forms a part of a projected image of the subject;

a diffraction grating configured to be exposed to the radiation emitted from the multiple radiation sources of the radiation emission unit and to produce a Talbot effect by the exposure; and a periodic information imaging radiation image detector for detecting periodic information of the radiation diffracted by the diffraction grating.

In the second radiation phase image radiographing apparatus of the present invention, the multiple radiation sources may be disposed along a planar surface, and the diffraction grating and periodic information imaging radiation image detector may be formed respectively along planar surfaces parallel to the planar surface on which the multiple radiation sources are disposed.

Further, the multiple radiation sources may be disposed along a cylindrical surface, and the diffraction grating and periodic information imaging radiation image detector may be formed respectively along cylindrical surfaces concentric with the cylindrical surface on which the multiple radiation sources are disposed.

Still further, the multiple radiation sources or the periodic information imaging radiation image detector may be disposed in abutment with a cylindrical surface centered on a position where the subject is placed, and the diffraction grating may be formed in abutment with a cylindrical surface concentric with the cylindrical surface to which the multiple radiation sources or the periodic information imaging radiation image detector is abutted.

Further, each of the multiple radiation sources may be a radiation source that emits radiation such that exposure areas of radiation emitted from adjacent radiation sources at a position of the subject overlap with each other without any space between them and at an angle that substantially does not influence diffraction properties of the diffraction grating and periodic information imaging radiation image detector in peripheral portions of exposure areas at positions of the diffraction grating and periodic information imaging radiation image detector.

Still further, a spread angle of the radiation emitted from each of the multiple radiation sources in an extending direction of a diffraction member of the diffraction grating may be made larger than a spread angle of the radiation in a direction orthogonal to the extending direction.

Further, an arrangement area of the multiple radiation sources in an extending direction of a diffraction member of the diffraction grating may be made smaller than an arrangement area of the radiation sources in a direction orthogonal to the extending direction.

Still further, all of the multiple radiation sources may be disposed in a line in a direction orthogonal to the extending direction of the diffraction member of the diffraction grating.

Further, each radiation source may be a micro-focus X-ray source, and a Talbot interferometer may be constructed with the diffraction grating and periodic information imaging radiation image detector.

Still further, each radiation source may be an X-ray source constituted by an electron source, a metal target, and a slit made of linear members parallel to diffraction members of the diffraction grating and transmits an X-ray emitted from the metal target, and a Talbot-Lau interferometer may be constructed with the diffraction grating and periodic information imaging radiation image detector.

Further, a phase image may be formed based on image signals corresponding to a plurality of phase components detected by the periodic information imaging radiation image detector without shifting the diffraction grating and periodic information imaging radiation image detector in a direction orthogonal to the extending direction of a diffraction member of the diffraction grating.

Still further, a partial phase image may be generated with respect to each detection area of the periodic information imaging radiation image detector corresponding to an exposure area of the radiation emitted from each radiation source based on image signals corresponding to a plurality of phase components, each detected by each detection area, and a complete phase image may be formed by combining the partial phase images.

Further, among image signals detected by the periodic information imaging radiation image detector, only a signal detected by a detection area of the periodic information imaging radiation image detector corresponding to an exposure area of the radiation emitted from each radiation source and propagated straightly may be extracted.

According to the first and second radiation phase image radiographing apparatuses of the present invention, the radiation emission unit is formed of multiple radiation sources, and the multiple radiation sources are distributed such that radiation emitted from each radiation source and transmitted through the subject forms a part of a projected image of a subject. This may reduce the spread angle of the radiation emitted from each radiation source in a direction orthogonal to an extending direction of the diffraction members, so that radiation is allowed to pass through not only a center portion but also other portions of the diffraction grating and large-size radiation phase imaging becomes possible.

Further, in the first and second radiation phase image radiographing apparatuses, when the multiple radiation sources are disposed along a cylindrical surface and the diffraction gratings or grating is formed along a cylindrical surface concentric with the surface on which the multiple radiation sources are disposed, the overall size of the radiation emission unit may be reduced.

Still further, when the multiple radiation sources or the radiation image detector is disposed in abutment with a cylindrical surface centered on a position where a subject is placed, and the diffraction gratings are formed respectively in abutment with a cylindrical surface concentric with the cylindrical surface to which the multiple radiation sources or the radiation image detector is abutted, a three-dimensional image may be obtained by rotating them.

Further, when each of the multiple radiation sources is configured to emit radiation such that exposure areas of radiation emitted from adjacent radiation sources at a position of the subject overlap with each other without any space between them and at an angle that substantially does not influence diffraction property of the diffraction grating in a peripheral portion of an exposure area at a position of the diffraction grating, an appropriate phase image without any space may be obtained.

Still further, when a spread angle of the radiation emitted from each of the multiple radiation sources in an extending direction of a diffraction member of the diffraction grating is made larger than a spread angle of the radiation in a direction orthogonal to the extending direction, for example, a radiation source that emits a fan beam may be used as the radiation source, which is more advantageous in terms of utilization efficiency of radiation than a radiation source that emits a pencil beam.

Further, if an arrangement area of the multiple radiation sources in an extending direction of a diffraction member of the diffraction grating is made smaller than an arrangement area of the radiation sources in a direction orthogonal to the extending direction, the size of the radiation emission unit may be reduced and the overall size of the apparatus may be reduced.

Still further, when all of the multiple radiation sources are disposed in a line in the direction orthogonal to the extending direction of the diffraction member of the diffraction grating, the size of the apparatus may further be reduced.

Further, among image signals detected by the radiation image detector, if only a signal detected by a detection area of the radiation image detector corresponding to an exposure area of radiation emitted from each radiation source and propagated straightly is extracted, influences of scattered radiation due to a subject may be eliminated, and the image quality of a phase image may be improved.

According to the second radiation phase image radiographing apparatus of the present invention, a periodic information imaging radiation image detector is used as the detector. This may eliminate the need to provide an amplitude diffraction grating as in a conventional radiation phase image radiographing apparatus, which facilitates the manufacture of the apparatus with reduced cost.

BRIEF DESCRIPTION OF THE DRAWINGS

FIG. 31 illustrates a structure of linear electrodes of periodic information imaging radiation image detector in the third embodiment of the radiation phase image radiographing apparatus of the present invention.

FIGS. 32A and 32B illustrate a recording operation for recording a radiation image in the periodic information imaging radiation image detector in the third embodiment of the radiation phase image radiographing apparatus of the present invention.

DESCRIPTION OF THE PREFERRED EMBODIMENTS

Figure 1:
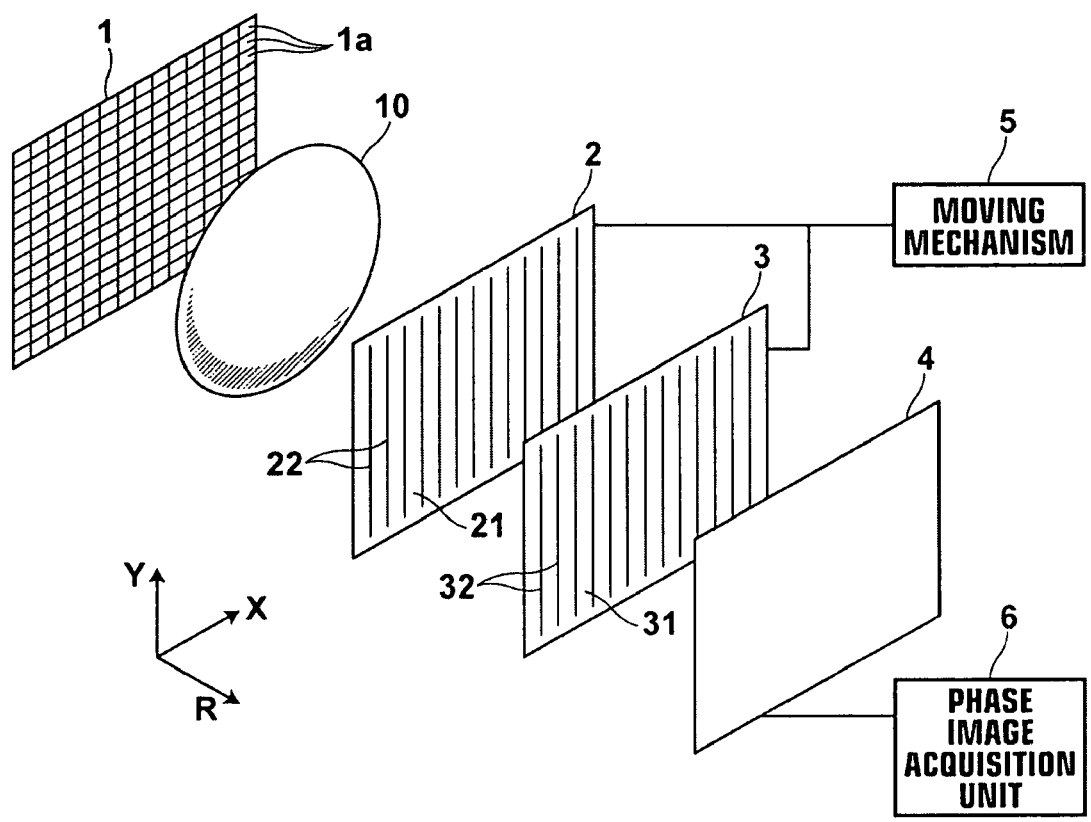
FIG. 1 is a schematic construction diagram of a first embodiment of the radiation phase image radiographing apparatus of the present invention.
Figure 2:
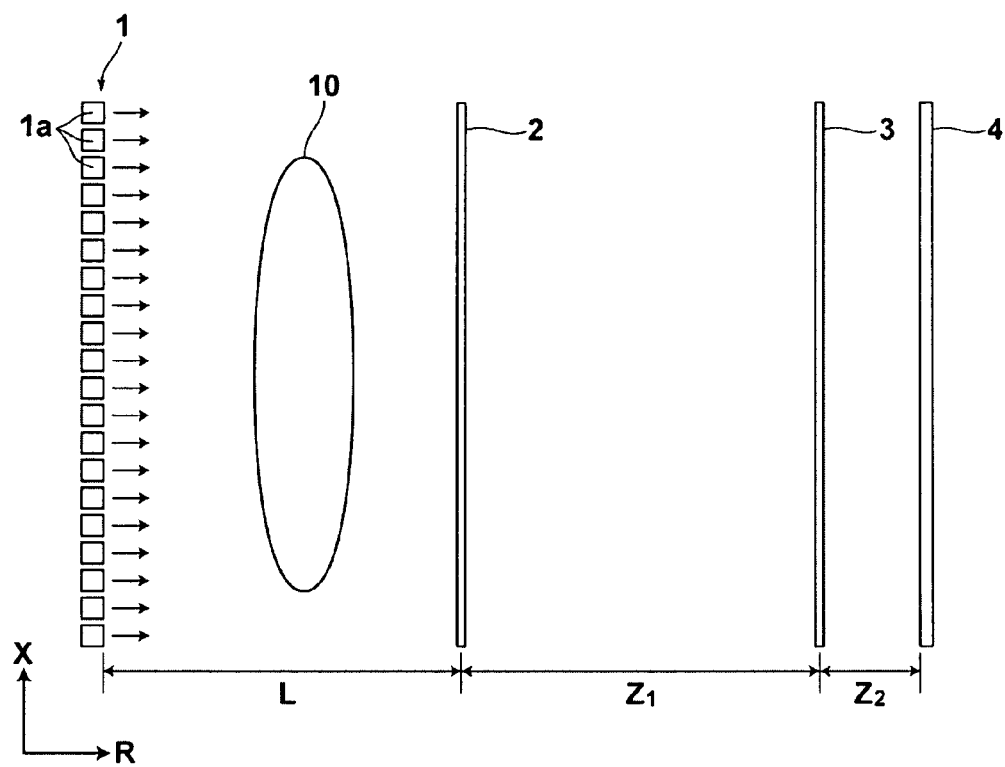
FIG. 2 is a top view of the radiation phase image radiographing apparatus shown in FIG. 1.

Hereinafter, a first embodiment of the radiation phase image radiographing apparatus of the present invention will be described with reference to the accompanying drawings. A schematic construction of the radiation phase image radiographing apparatus according to the first embodiment is shown in FIG. 1. FIG. 2 is a top view (XR cross-section) of the radiation phase image radiographing apparatus shown in FIG. 1. The thickness direction in FIG. 2 corresponds to Y direction in FIG. 1.

As illustrated in FIG. 1, the radiation phase image radiographing apparatus includes radiation emission unit 1 that emits radiation onto subject 10, first diffraction grating 2 configured to be exposed to the radiation transmitted through subject 10 and to produce a Talbot effect by the exposure, second diffraction grating 3 for diffracting the radiation diffracted by first diffraction grating 2, radiation image detector 4 for detecting the radiation diffracted by second diffraction grating 3, shifting mechanism 5 for shifting first diffraction grating 2 and second diffraction grating 3 in a direction orthogonal to diffraction members (X direction in FIG. 1) along the respective planes, and phase image acquisition unit 6 for forming a phase image based on an image signal detected by radiation image detector 4.

As shown in FIG. 1, radiation emission unit 1 includes multiple radiation sources 1a, each for emitting radiation, disposed two-dimensionally along a planar surface. The radiation emitted from each radiation source 1a transmits through a subject and detected by radiation image detector 4. Each of radiation sources 1a is distributed such that the radiation emitted from each radiation source 1a and transmitted through the subject forms a part of a projected image of the subject. That is, a complete projected image is formed by combining partial projected images of the subject formed by the radiation emitted from each radiation source 1a.

It is assumed that radiation source 1a has spatial coherence sufficient to produce a Talbot effect when first diffraction grating 2 is exposed to the radiation. For example, when the size of the radiation emission point (aperture diameter of radiation source) is set to about 30 μm, and spatial coherence at a position 5m or more away from the radiation source corresponds the spatial coherence described above. In the present embodiment, a micro focus X-ray source with a cold cathode electron source or a plasma X-ray source may be used as radiation source 1a. Preferably, the number of radiation sources 1a corresponds to the number of pixels of radiation image detector 4, but not limited to this arrangement.

Preferably, each of multiple radiation sources 1a of radiation emission unit 1 is a radiation source that emits radiation such that exposure areas of adjacent radiation sources at a position of subject 10 overlap with each other without any space between them and at an angle that substantially does not influence the diffraction property of first diffraction grating 2 in a peripheral portion of exposure area at the position of first diffraction grating 2. Conditions of the angle will be described in detail later.

In the present invention, radiation emission unit 1 may have another structure, which will be described in detail later.

Figure 3:
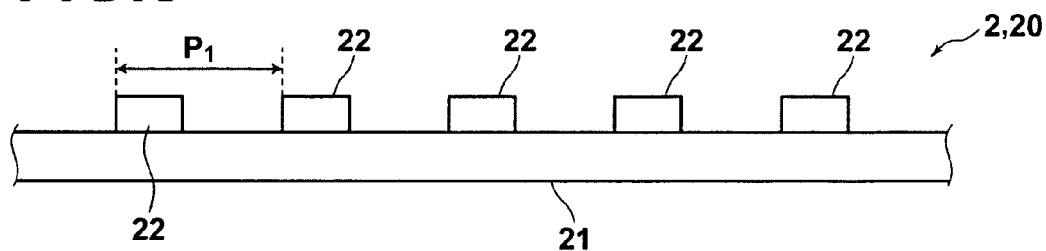
FIG. 3 is a schematic construction diagram of a first diffraction grating.

First diffraction grating 2 is formed along a planar surface parallel to the planar surface on which multiple radiation sources 1a are disposed. As shown in FIG. 3, first diffraction grating 2 includes substrate 21 and a plurality of diffraction members 22 provided on substrate 21. Each of the plurality of diffraction members 22 is formed in a linear shape extending in one direction (thickness direction in FIG. 3). Spacing $P_1$ between each of the plurality of diffraction members 22 (the period of the diffraction grating) is constant in the present embodiment. As for the material of diffraction member 22, for example, gold may be used. Preferably, diffraction member 22 forms a so-called phase diffraction grating that phase modulates the emitted radiation by about 80 to 100° (ideally, 90°). The thickness of gold required in the X-ray energy range of ordinary medical diagnosis is about one to several micrometers.

Figure 4:
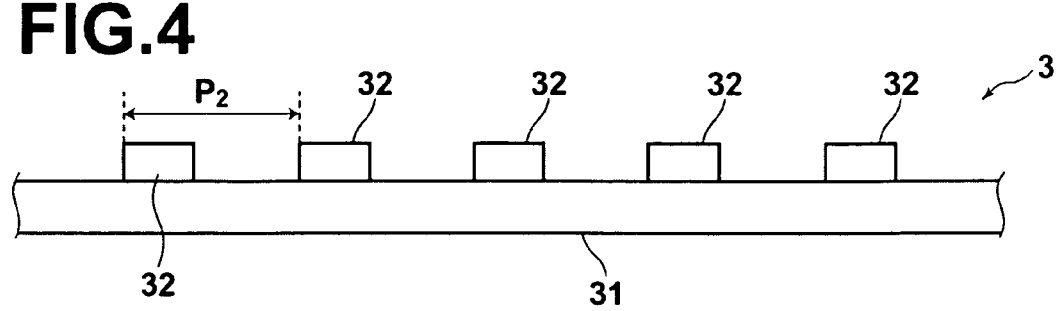
FIG. 4 is a schematic construction diagram of a second diffraction grating.

Second diffraction grating 3 is formed along a planar surface parallel to the planar surface on which multiple radiation sources 1a are disposed. As shown in FIG. 4, second diffraction grating 3 includes substrate 31 and a plurality of diffraction members 32 provided on substrate 31, as in first diffraction grating 2. Each of the plurality of diffraction members 32 is formed in a linear shape extending in one direction (thickness direction in FIG. 4). Spacing $P_2$ between each of the plurality of diffraction members 32 (the period of the diffraction grating) is constant in the present embodiment. As for the material of diffraction member 32, for example, gold may be used. Second diffraction grating 3 is structured to form image contrast by diffracting the radiation diffracted by first diffraction grating 2. Preferably, second diffraction grating 3 is an amplitude diffraction grating having thicker diffraction members, but it may be constructed in the same manner as first diffraction grating 2. In order to make second diffraction grating 3 as an amplitude diffraction grating, the diffraction members need to sufficiently absorb radiation. The thickness of gold required in the X-ray energy range of ordinary medical diagnosis is around ten to several tens of micrometers.

The ratio between distance L from radiation source 1a to first diffraction grating 2 and pitch $P_1$ in first diffraction grating 2 may be set substantially equal to the ratio between distance from radiation source 1a to second diffraction grating 3, L+Z1 and pitch $P_2$ in second diffraction grating 3.

Radiation image detector 4 is a detector that detects the radiation having image contrast produced by first diffraction grating 2 and second diffraction grating 3. Radiation image detector 4 may be an identical detector used in a conventional radiation phase image radiographing apparatus, such as a direct conversion or indirect conversion flat panel detector, an imaging plate, an intensifying screen-film combination, or the like. Therefore, it will not be elaborated upon further here.

A Talbot interferometer is constructed with radiation source 1a, first diffraction grating 2, and second diffraction grating 3. Conditions for constructing the Talbot interferometer will be described.

First, coherence length l is calculated in the following manner.

$$l = \frac{\lambda}{a/(L+Z_1+Z_2)} \quad (1)$$

where,

λ: wavelength of radiation (generally, center wavelength)
a: aperture diameter of radiation source 1a in a direction substantially orthogonal to diffraction members.
L: distance from radiation source 1a (if a slit is used in the radiation emission unit, to be described later, from the position of the slit) to first diffraction grating 2 (FIG. 2)
$Z_1$: distance from first diffraction grating 2 to second diffraction grating 3 (FIG. 2)
$Z_2$: distance from second diffraction grating 3 to radiation image detector 4 (FIG. 2)

Distance $Z_1$ between first diffraction grating 2 and second diffraction grating 3 needs to substantially satisfy the following conditions, on the assumption that first diffraction grating 2 is a phase diffraction grating.

$$Z_1 = \left(m + \frac{1}{2}\right)\frac{P_1^2}{\lambda} \quad (2)$$

where, m is an integer, $P_1$ is the period of the diffraction members described above.

$$Z_1 = (m+1)\frac{P_1^2}{\lambda} \quad (3)$$

where, m is 0 or a positive integer, and λ is the wavelength of radiation.

As described above, shifting mechanism 5 is a mechanism for shifting first and second diffraction gratings 2, 3 in X direction. For example, first and second diffraction gratings 2, 3 may be shifted by 1/n (n is an integer not less than two) of pitch $P_1$ of the first diffraction members and take a radiation image at each position, whereby image signals of n-types of phase components may be obtained. It is preferable, for example, to shift first and second diffraction gratings 2, 3 such that image signals corresponding to four or six types of phase components are obtained.

An operation of the radiation phase image radiographing apparatus according to the present embodiment will now be described.

First, as illustrated in FIG. 1, subject 10 is placed between radiation emission unit 1 and first diffraction grating 2. Then, radiation is emitted from each radiation source 1a of radiation emission unit 1 at the same time onto first diffraction grating 2. The radiation emitted on first diffraction grating 2 passes through first diffraction grating 2. At this time, a Talbot effect is produced in first diffraction grating 2.

The Talbot effect as used herein refers to that, when a plane wave passes through a phase diffraction grating, a self-image of the diffraction grating is formed at the distance given by Formula (2) above. In the case described above, the radiation is phase shifted by subject 10, so that the wave front of the radiation incident on first diffraction grating 2 is distorted. Accordingly, the self-image of first diffraction grating 2 is deformed according to the distortion. Then, the radiation passes through second diffraction grating 3. As a result, the deformed self-image of first diffraction grating 2 and second diffraction grating 3 are superimposed with each other, whereby image contrast may be generated in the radiation. The image contrast generally takes the form of Moire fringes and can be detected by radiation image detector 4. The generated Moire fringes are modulated by subject 10. The amount of modulation is proportional to the angle by which the radiation is bent due to the refraction effect of subject 10. Therefore, subject 10 and internal structures of the subject may be detected by analyzing the Moire fringes detected by radiation image detector 4.

Then, an image signal corresponding to a phase component when first and second diffraction gratings 2, 3 are placed at a predetermined position in the manner as described above is detected by radiation image detector 4. Then, first and second diffraction gratings 2, 3 are shifted by shifting mechanism 5 in X direction by 1/n (n is an integer not less than two) of pitch $P_1$ of the first diffraction members, and an image signal corresponding to the phase component at each position is detected by radiation image detector 4.

Image signals detected in the manner as described above are inputted to phase image acquisition unit 6. Then, phase image acquisition unit 6 generates a partial phase image with respect to each detection area of radiation image detector 4 based on image signals of a plurality of phase components detected by radiation image detector 4 in each detection area corresponding to the exposure area of radiation emitted from each radiation source 1a. That is, a partial phase image corresponding to each radiation source 1a is generated. Thereafter, the partial phase images are combined to produce a complete phase image.

As described above, it is preferable that each radiation source 1a emits radiation such that the exposure area at the position of subject 10 is arranged without any space and at an angle that substantially does not influence the diffraction properties of first diffraction grating 2 and second diffraction grating 3 at peripheral portions of the exposure areas at the positions of first diffraction grating 2 and second diffraction grating 3. Hereinafter, the angle will be discussed. Here, the allowable range of the angle will be discussed in terms of the positional displacement of first diffraction grating 2.

Figure 5:
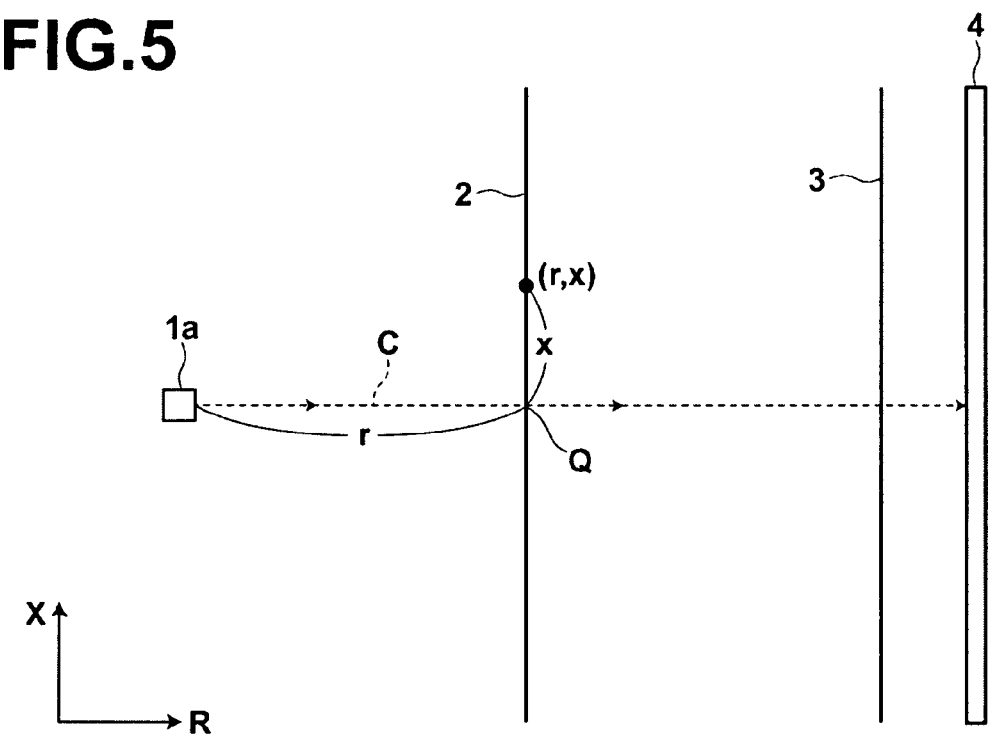
FIG. 5 illustrates conditions of spread angle of radiation emitted from a radiation source.

Assuming a required pitch of diffraction members at a position (r, x) away from intersection point Q between central axis C of the radiation emitted from radiation source 1a and first diffraction grating 2 by distance x in a direction orthogonal to the diffraction members to be $\Delta x$, $\Delta x$ can be represented by Formula (4) below (FIG. 5, which is a top view of the radiation phase image radiographing apparatus shown in FIG. 1. The thickness direction in FIG. 5 corresponds to Y direction in FIG. 1.)

$$\Delta x = r\Delta\theta \times \frac{\tan\theta}{\theta} \times \left\{\sqrt{(r^2 + x^2)} \times \frac{1}{r}\right\} \times \frac{1}{\cos\theta} \quad (4)$$

where, r is the distance from radiation source 1a (if a slit is used in the radiation emission unit, to be described later, from the position of the slit) to first diffraction grating 2, and $r\Delta\theta$ is the pitch of the diffraction members at intersection point Q between the central axis C of the radiation beam and first diffraction grating.

Here, $x/r=\tan\theta$, which is substituted to Formula (4) above, then $\Delta x$ can be represented by Formula (5) below.

$$\Delta x = r\Delta\theta \times \frac{\tan\theta}{\theta} \times \frac{\sqrt{1 + \tan^2\theta}}{\cos\theta} = r\Delta\theta \times \frac{\tan\theta}{\theta\cos^2\theta} \quad (5)$$

Thus, the ratio between the pitch at (r, x) and the pitch $r\Delta\theta$ at intersection point Q can be represented by Formula (6) below.

$$\frac{\Delta x}{r\Delta\theta} = \frac{\tan\theta}{\theta\cos^2\theta} \quad (6)$$

Relationship between $\theta$ and $\Delta x/r\Delta\theta$ obtained based on Formula (6) above is summarized in Table 1 below.

TABLE 1

| | θ | | | | |
|---|---|---|---|---|---|
| | 1.0° | 2.0° | 5.0° | 10.0° | 15.0° |
| Δx/rΔθ | 1.0004 | 1.002 | 1.01 | 1.04 | 1.10 |

Here, assuming pitch $P_1$ of the diffraction members of first diffraction grating 2 to be 0.8 μm, the width of each diffraction member to be 3 μm, and one pixel width of radiation image detector 4 to be 120 μm, if the phase of first diffraction grating 2 is shifted about 1/12 of the pitch, it is thought to be undesirable that a signal of different phase component is mixed in the same pixel. Given that the radiation beam spreads from the central axis to X direction (direction orthogonal to the diffraction members), it is preferable that the positional displacement is limited to 8/12×1/2=8/24=0.333 μm or less.

That is, if the pitch of the diffraction members on central axis C is assumed to be 8 μm, the distance between the centers of diffraction members at each end in one pixel in a peripheral portion of the radiation beam is $\Delta x/r\Delta\theta \times 8 \times 4$.

Accordingly, if $\Delta x/r\Delta\theta \times 8 \times 4 - 32 < 0.333$, the condition described above is met.

Thus, $\Delta x/r\Delta\theta < 1.010$.

Accordingly, it is known from Table 1 above that one-side spread angle $\theta$ of the radiation beam in X direction needs to be limited to 5° or less.

For example, if r=1000 mm, 2×1000×tan 5°=175 mm, thus the width of radiation beam emitted from one radiation source 1a in X direction on first diffraction grating 2 needs to be limited to 175 mm or less.

So far, the description has been made of a case in which one pixel width of radiation image detector 4 is assumed to be about 120 μm. Now, the discussion will be made of a case in which one pixel width of radiation image detector 4 is assumed to be about 80 μm. Here, the pitch and width of the diffraction members are assumed to be identical to those described above.

When the phase of first diffraction grating 2 is shifted about 1/8 of the pitch, it is thought to be undesirable that a signal of different phase component is mixed in the same pixel. Given that the radiation beam spreads from the central axis to X direction (direction orthogonal to the diffraction members), it is preferable that the positional displacement of diffraction members in one pixel is limited to 8/8×1/2=8/16=0.5 μm or less.

That is, if the pitch of the diffraction members on central axis C is assumed to be 8 μm, the distance between the centers of diffraction members at each end in one pixel in a peripheral portion of the radiation beam is $\Delta x/r\Delta\theta \times 8 \times 4$.

Accordingly, if $\Delta x/r\Delta\theta \times 8 \times 4 - 32 < 0.5$, the condition described above is met.

Thus, $\Delta x/r\Delta\theta < 1.016$.

Accordingly, it is known from Table 1 above that one-side spread angle $\theta$ of the radiation beam in X direction needs to be limited to 6° or less.

For example, if r=1000 mm, 2×1000×tan 6°=210 mm, thus the width of the radiation beam emitted from one radiation source 1a in X direction on first diffraction grating 2 needs to be limited to 210 mm or less.

The above discussion shows that the pitch of the diffraction members is not restricted by spread angle $\theta$ of the radiation beam.

In the discussion above, the description has been made of a case in which subject 10 is placed between radiation emission unit 1 and first diffraction grating 2. Also, in a case in which subject 10 is placed between first diffraction grating 2 and second diffraction grating 3, the self-image of first diffraction grating 2 produced at the position of second diffraction grating 3 is deformed by subject 10. Therefore, also in this case, an image signal of a phase component modulated due to subject 10 can be detected by radiation image detector 4. That is, in the radiation phase image radiographing apparatus according to the present embodiment, subject 10 may be placed between radiation emission unit 1 and first diffraction grating 2 or between first diffraction grating 2 and second diffraction grating 3.

Next, a modification of the radiation phase image radiographing apparatus according to the first embodiment of the present invention will be described.

Figure 6:
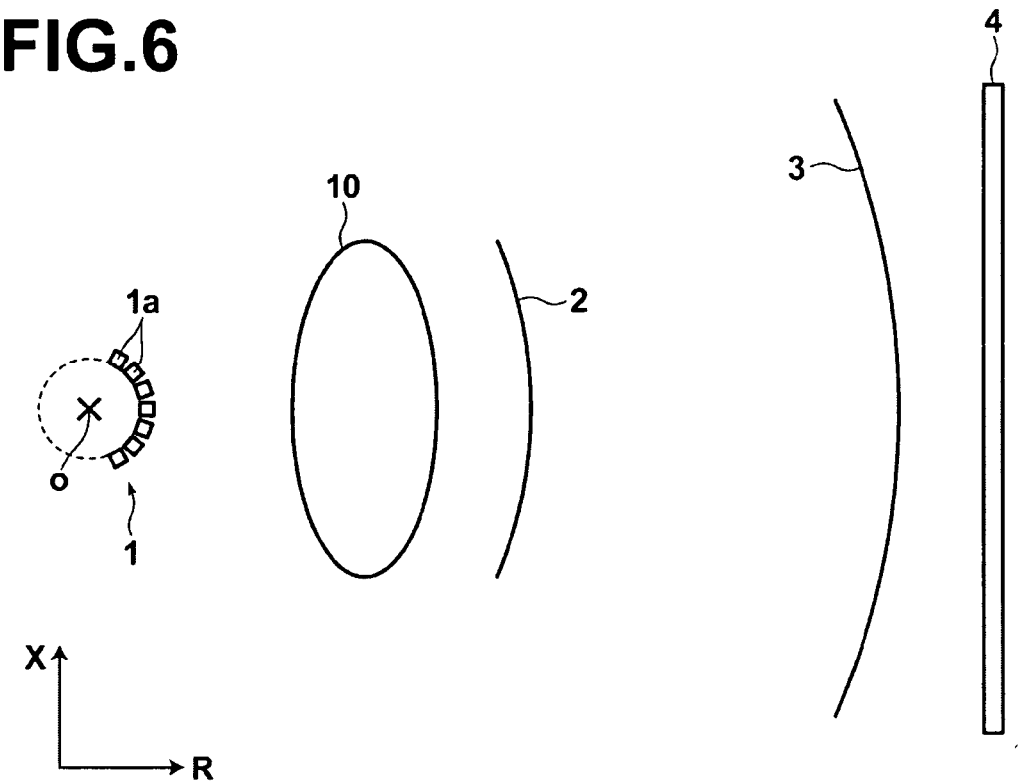
FIG. 6 is a schematic construction diagram of a radiation phase image radiographing apparatus in which radiation sources are disposed on a cylindrical surface.

In the radiation phase image radiographing apparatus according to the first embodiment, radiation sources 1a are disposed along a planar surface, and first diffraction grating 2 and second diffraction grating 3 are formed along planar surfaces parallel to the planar surface on which multiple radiation sources 1a are disposed. But the structure is not limited to this, and an arrangement may be adopted in which radiation sources 1a are disposed along a cylindrical surface to form radiation emission unit 1, and first diffraction grating 2 and second diffraction grating 3 are formed along cylindrical surfaces concentric with the center O of the cylindrical surface on which multiple radiation sources 1a are disposed, as illustrated in FIG. 6. The arrangement of the radiation sources 1a along a cylindrical surface in the manner as described above may reduce the overall size of radiation emission unit 1 in comparison with the case in which radiation sources 1a are disposed along a planar surface as in the first embodiment, whereby downsizing of the apparatus may be achieved.

In this case, conditions of forming a Talbot interferometer depend on the distance from each radiation source 1a.

When forming first diffraction grating 2 and second diffraction grating 3 along cylindrical surfaces, for example, transparent flexible substrates may be used as substrates 21 and 31, then diffraction members 22, 32 are formed on the flexible substrates, and the flexible substrates may be bonded to base materials having the cylindrical surfaces. Alternatively, thin glass substrates reinforced with a plastic film may be used as substrates 21 and 31, then diffraction members 22, 32 are formed on the reinforced glass substrates, and the reinforced glass substrates may be bonded to base materials having the cylindrical surfaces.

Further, radiation image detector 4 may be formed along a cylindrical surface concentric with the center O of the cylindrical surface on which multiple radiation sources 1a are disposed.

Still further, radiation phase image radiographing apparatuses according to the first embodiment and modification may be applied to X-ray phase CT systems. More specifically, as illustrated in FIG. 7, a rotation mechanism for integrally rotating radiation emission unit 1, first and second diffraction gratings 2, 3, and radiation image detector 4 in the arrow direction in FIG. 7 with respect to subject 10 placed between radiation emission unit 1 and radiation image detector 4 may be provided, and a three-dimensional image is formed in three-dimensional image forming unit 400 based on a plurality of image data of subject 10 detected by radiation image detector 4 according to the rotation implemented by the rotation mechanism.

Figure 7:
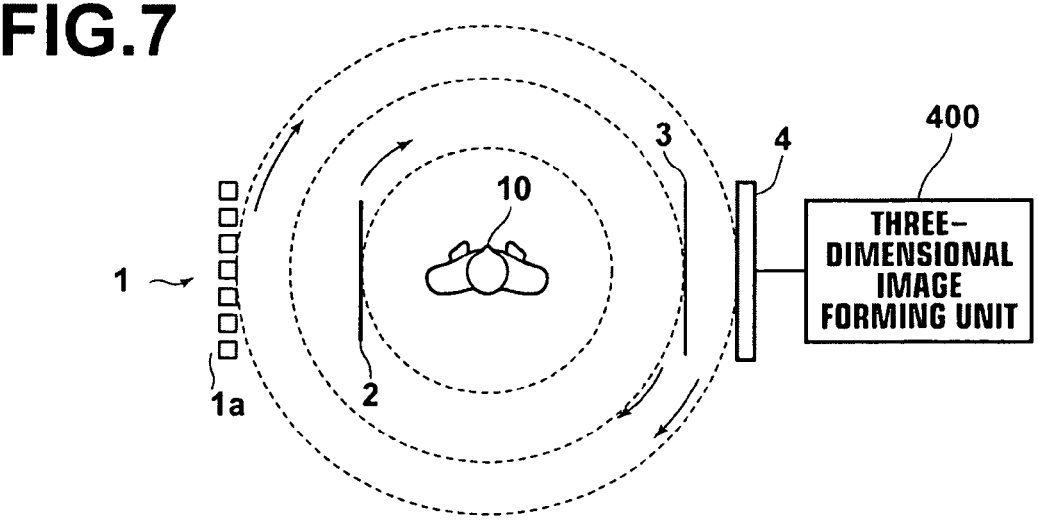
FIG. 7 is a schematic construction diagram of an X-ray phase CT system incorporating the radiation phase image radiographing apparatus according to the first embodiment or a modification thereof.
Figure 8:
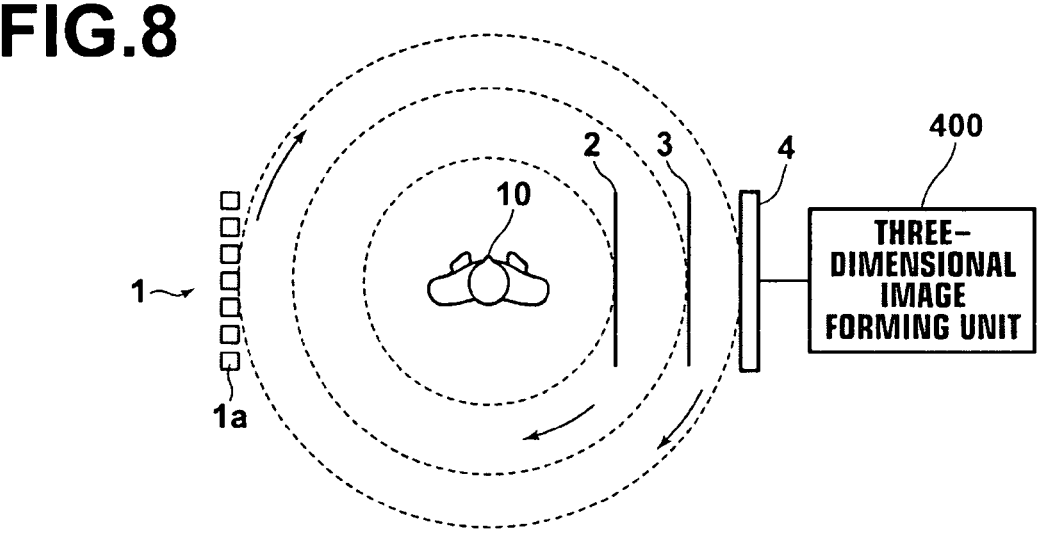
FIG. 8 is a schematic construction diagram of an X-ray phase CT system incorporating the radiation phase image radiographing apparatus according to the first embodiment or a modification thereof.

Subject 10 may be placed between first diffraction grating 2 and second diffraction grating 3, as illustrated in FIG. 7, or between radiation emission unit 1 and first diffraction grating 2, as illustrated in FIG. 8. Note that FIGS. 7 and 8 illustrate only the positional relationships among radiation emission unit 1, first and second diffraction gratings 2 and 3, radiation image detector 4, and subject 10, and do not accurately represent distances from radiation emission unit 1 to first and second diffraction gratings 2 and 3, and distances from first and second diffraction gratings 2 and 3 to radiation image detector 4. The distances from radiation emission unit 1 to first and second diffraction gratings 2 and 3, and distances from first and second diffraction gratings 2 and 3 to radiation image detector 4 are set so as to satisfy the conditions for obtaining Talbot effect.

The method of forming a three-dimensional image based on a plurality of image data of subject 10 detected by radiation image detector 4 is identical to that of a conventional X-ray phase CT system.

In X-ray phase CT systems shown in FIGS. 7 and 8, radiation emission unit 1, first and second diffraction gratings 2 and 3, and radiation image detector 4 are integrally rotated, but radiation emission unit 1 or radiation image detectors 4 may be fixedly arranged over the entire circumference along a cylindrical surface centered on the position where subject 10 is placed.

Figure 9:
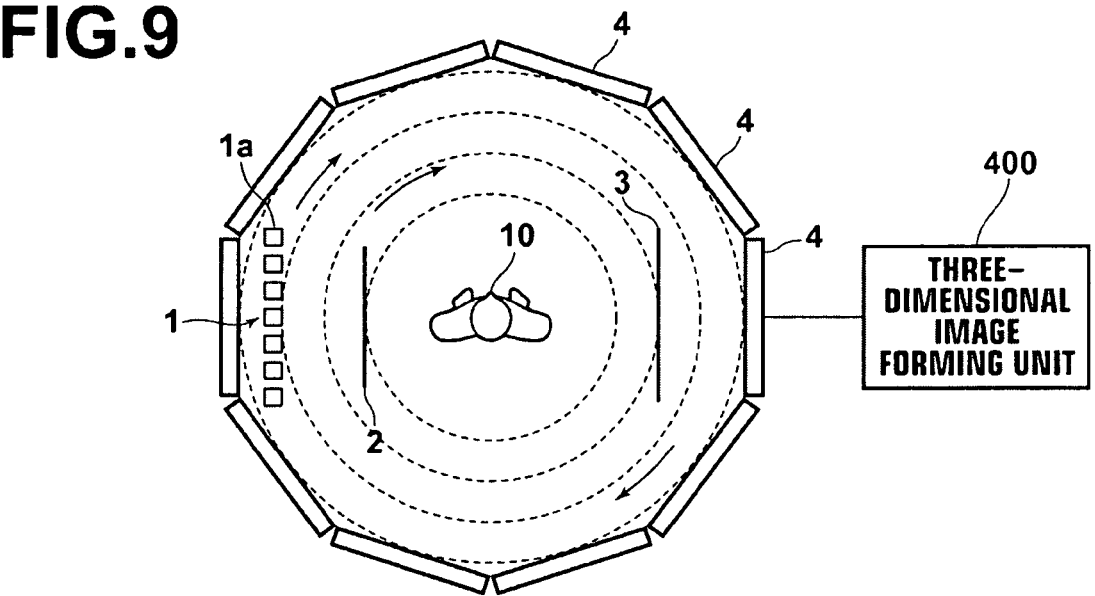
FIG. 9 is a schematic construction diagram of a radiation phase image radiographing apparatus in which radiation image detectors are disposed along the entire circumference of a cylindrical surface centered on a subject.

FIG. 9 shows a configuration in which radiation image detectors 4 are disposed over the entire circumference of the cylindrical surface. In the configuration shown in FIG. 9, radiation emission unit 1, first diffraction grating 2, and second diffraction grating 3 are integrally rotated centered on subject 10.

Figure 10:
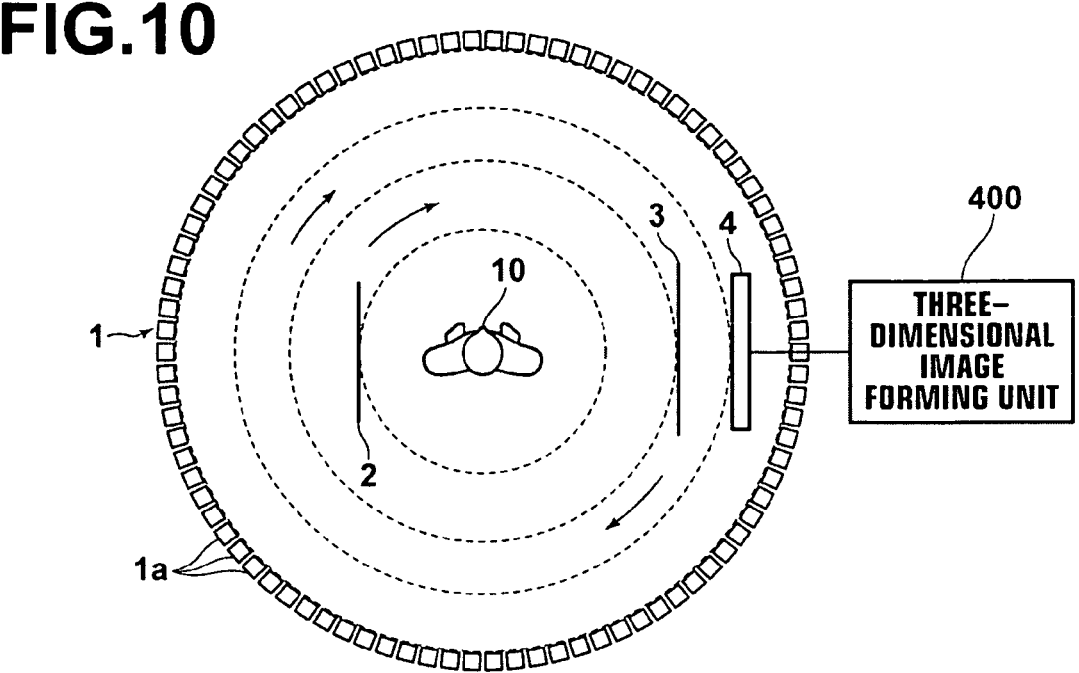
FIG. 10 is a schematic construction diagram of a radiation phase image radiographing apparatus in which radiation sources are disposed along the entire circumference of a cylindrical surface centered on a subject.

FIG. 10 shows a configuration in which each radiation source 1a of radiation emission unit 1 is disposed over the entire circumference of the cylindrical surface. In the configuration shown in FIG. 10, radiation image detector 4, first diffraction grating 2, and second diffraction grating 3 are integrally rotated centered on subject 10.

Figure 11:
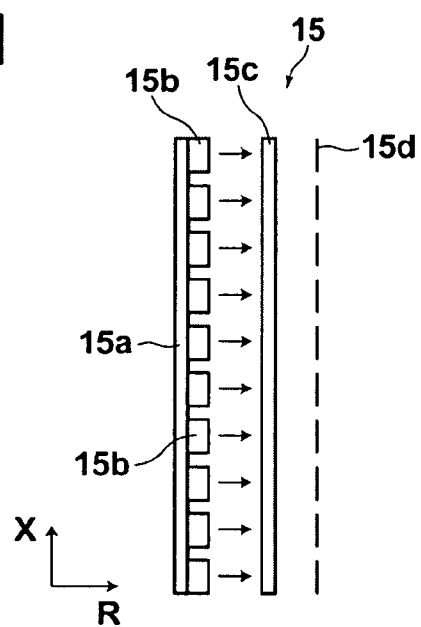
FIG. 11 illustrates an alternative embodiment of the radiation emission unit.

In the first embodiment, a micro focus X-ray source with a cold cathode electron source or a plasma X-ray source is used as each radiation source 1a constituting radiation emission unit 1. The structure of radiation emission unit 1 is not limited to this. For example, as illustrated in FIG. 11, radiation emission unit 15 may be formed of cold cathode electron source 15a, metal target 15c, and slit 15d formed of a slit member parallel to the diffraction members of first and second diffraction gratings 2 and 3 and transmits radiation emitted from metal target 15c.

Cold cathode electron source 15a, metal target 15c, and slit 15d are formed in a size corresponding to the size of radiation image detector 4.

As for cold cathode electron source 15a, for example, an electron source of a FED (Field Emission Display) or a SED (Surface-conduction Electron-emitter Display) may be used. Cold cathode electron source 15a includes multiple electron emission units 15b that emit electrons. Preferably, electron emission unit 15b is provided with respect to each pixel of radiation image detector 4, but not limited to this.

Slit 15d restricts the irradiation range of the radiation emitted from metal target 15c by the collision of electrons emitted from each electron emission unit 15b. More specifically, it is preferable that slit 15d restricts exposure areas of radiation such that exposure areas of the radiation transmitted through slit 15d at the position of subject 10 overlap with each other without any space between them and radiation transmitted through slit 15d is incident on a peripheral portion of the exposure areas at the position of first diffraction grating 2 at an angle that substantially does not influence the diffraction property of first diffraction grating 2.

In radiation emission unit 15 shown in FIG. 11, metal target 15c may be formed of metal wires, instead of a flat material, parallel to diffraction members 22 and 32 of first and second diffraction gratings 2 and 3, thereby eliminating slit 15d. In this case, the conditions of desirable radiation exposure areas are identical to those described above.

Further, in radiation emission unit 15 shown in FIG. 11, cold cathode electron source 15a may be formed of linear cold cathode electron sources, instead of a flat source, parallel to diffraction members 22 and 32 of first and second diffraction gratings 2 and 3, thereby eliminating slit 15d. In this case, the conditions of desirable exposure areas of radiation are identical to those described above.

When the structure shown in FIG. 11 and modifications thereof described above are used, Talbot-Lau interferometers are formed.

Only the spreading of radiation in a direction orthogonal to the extending direction of diffraction members 22 of first diffraction grating 2 is involved in the interference condition for constructing the Talbot interferometer and Talbot-Lau interferometer, and the spreading of radiation in the extending direction of diffraction member 22 is not involved in the interference condition. Consequently, an emission unit that emits a fan beam having a larger spread angle in the extending direction of diffraction member 22 than that in a direction orthogonal to the extending direction of diffraction member 22 may be used as the radiation emission unit. The use of a fan beam is more advantageous in terms of utilization efficiency of radiation than the use of micro focus X-ray source.

Figure 12:
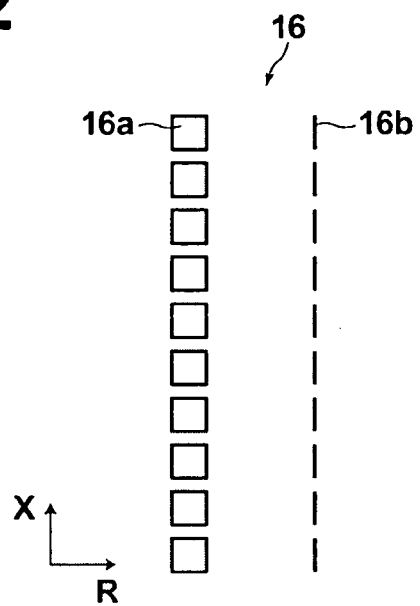
FIG. 12 illustrates an alternative embodiment of the radiation emission unit.

More specifically, a configuration may be adopted in which a plurality of radiation sources 16a, which emits the radiation more broadly than a micro focus X-ray source, is disposed in a line in X direction and exposure areas of radiation emitted from radiation sources 16 are limited by the openings of slit 16b, as illustrated in FIG. 12. The spread angle in the extending direction of diffraction member 22 is assumed to be set to an angle that allows radiation to be emitted over the entire radiation detector 4. The radiation source array is not limited to a single array, and a plurality of arrays may be provided as long as the arrangement range of the radiation sources in the extending direction of diffraction members 22 of first diffraction grating 2 is narrower than the arrangement range of the radiation sources in a direction orthogonal to the extending direction of diffraction members 22.

In the radiation phase image radiographing apparatus according to the first embodiment, a plurality of phase components is obtained with respect to each detection area of radiation image detector 4 corresponding to an exposure area of the radiation emitted from each radiation source 1a in phase image acquisition unit 6. Here, among signals detected by each detection area, only an image signal outputted from a detection area corresponding to an exposure area of the radiation emitted from each radiation source 1a and propagated straightly may be extracted. The detection area corresponding to the exposure area of the radiation outputted from each radiation source and propagated straightly may be set in advance by emitting radiation from each radiation source 1a without subject 10, and obtaining the exposure area (detection area) on radiation image detector 4. Extraction of image signal in the manner as described above allows elimination of scattered radiation influences and improvement in image quality.

Figure 13:
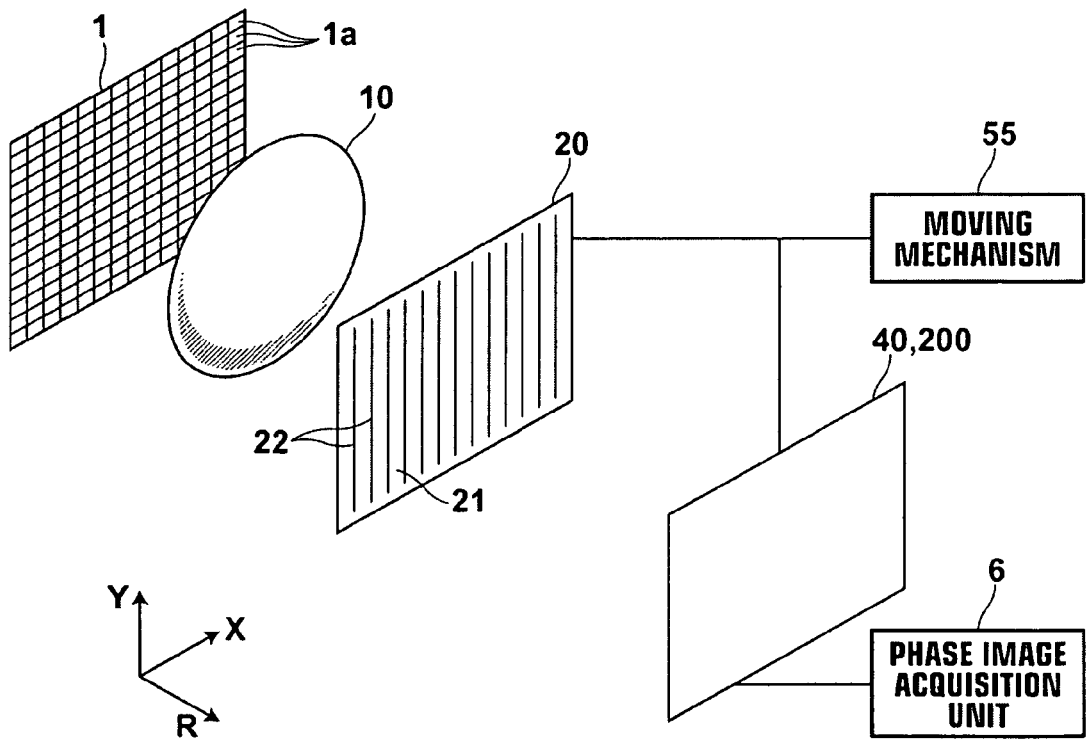
FIG. 13 is a schematic construction diagram of a second or a third embodiment of the radiation phase image radiographing apparatus of the present invention.
Figure 14:
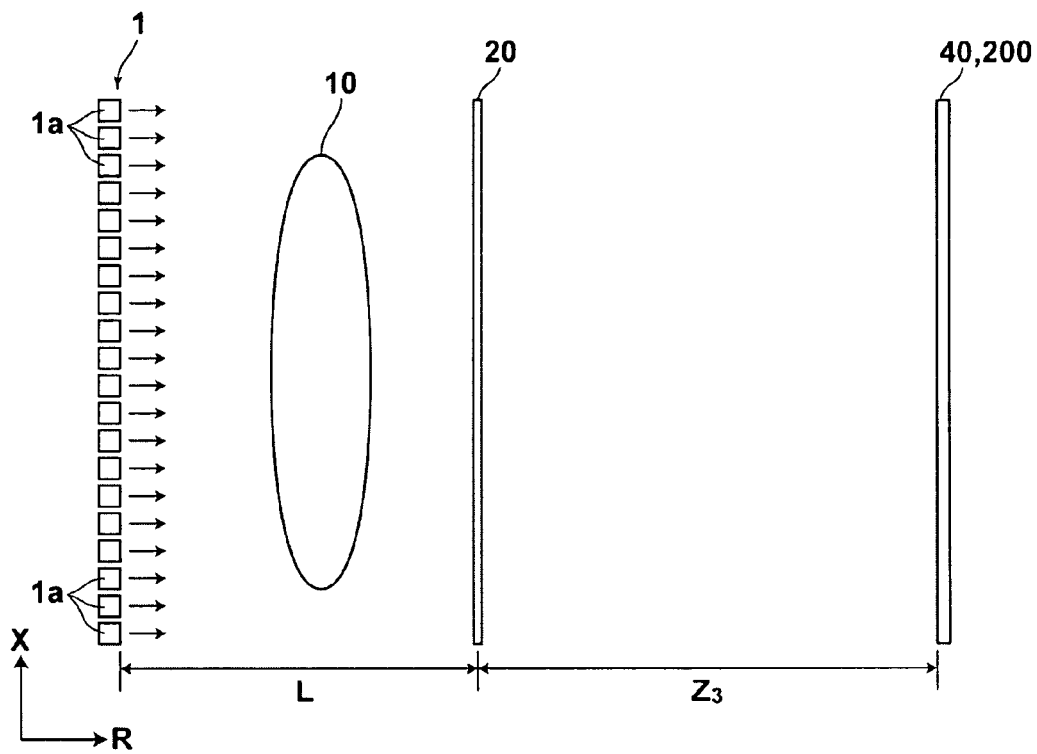
FIG. 14 is a top view of the radiation phase image radiographing apparatus shown in FIG. 13.

Next, a second embodiment of the radiation phase image radiographing apparatus of the present invention will be described. A schematic construction of the radiation phase image radiographing apparatus according to the second embodiment is illustrated in FIG. 13. FIG. 14 is a top view (XR cross-section) of the radiation phase image radiographing apparatus shown in FIG. 13. The thickness direction in FIG. 14 corresponds to Y direction in FIG. 13.

The radiation phase image radiographing apparatus according to the second embodiment does not use radiation image detector 4 and second diffraction grating 3 used in the radiation phase image radiographing apparatus according to the first embodiment, and instead uses periodic information imaging radiation image detector 40.

As illustrated in FIG. 13, the radiation phase image radiographing apparatus according to the second embodiment includes radiation emission unit 1 that emits radiation onto subject 10, diffraction grating 20 configured to be exposed to the radiation transmitted through subject 10 and to produce Talbot effect by the exposure, periodic information imaging radiation image detector 40 that detects periodic information of the radiation diffracted by diffraction grating 20, shifting mechanism 55 that shifts diffraction grating 20 and periodic information imaging radiation image detector 40 in a direction orthogonal to linear electrodes of detector 40 (X direction in FIG. 13) along respective planes, and phase image acquisition unit 6 that forms a phase image based on an image signal detected by periodic information imaging radiation image detector 40.

Radiation emission unit 1 has an identical structure to those of the first embodiment and the modifications thereof.

Diffraction grating 20 has an identical structure to that of the first diffraction grating in the radiation phase image radiographing apparatus according to the first embodiment.

In the radiation phase image radiographing apparatus according to the second embodiment, a Talbot interferometer is constructed with diffraction grating 20 and periodic information imaging radiation image detector 40. Conditions for constructing the Talbot interferometer will be described. First, coherence length l is calculated in the following manner.

$$l = \frac{\lambda}{a/(L+Z_3)} \quad (7)$$

where,
λ: wavelength of radiation (generally, center wavelength)
a: aperture diameter of radiation source in a direction substantially orthogonal to diffraction members.
L: distance from radiation source (if a slit is used in the radiation emission unit, to be described later, from the position of the slit) to diffraction grating 20 (FIG. 14)
$Z_3$: distance from diffraction grating 20 to periodic information imaging radiation image detector 40 (FIG. 14)

Distance $Z_3$ between diffraction grating 20 and periodic information imaging radiation image detector 40 needs to substantially satisfy the following condition, on the assumption that diffraction grating 20 is a phase diffraction grating.

$$Z_3 = \left(m + \frac{1}{2}\right)\frac{P_1^2}{\lambda} \quad (8)$$

where, m is 0 or a positive integer, and λ is the wavelength of radiation.

If diffraction grating 20 is an amplitude diffraction grating, the following condition needs to be satisfied.

$$Z_3 = (m+1)\frac{P_1^2}{\lambda} \quad (9)$$

where, m is 0 or a positive integer, and λ is the wavelength of radiation.

Figure 15:
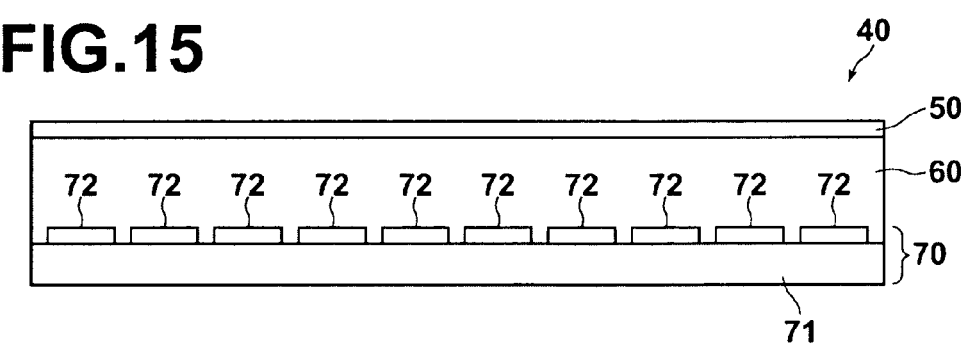
FIG. 15 is a cross-sectional view of periodic information imaging radiation image detector in the radiation phase image radiographing apparatus according to the second embodiment, illustrating a schematic construction thereof.

The structure of periodic information imaging radiation image detector 40 in the radiation phase image radiographing apparatus of the present embodiment will now be described in detail. FIG. 15 is a partial sectional view of periodic information imaging radiation image detector 40.

As illustrated in FIG. 15, periodic information imaging radiation image detector 40 includes active matrix substrate 70, semiconductor layer 60 formed on substantially the entire surface of the active matrix substrate 70, and upper electrode 50.

Semiconductor layer 60 has electromagnetic wave conductivity and generates charges therein when exposed to radiation. As for semiconductor layer 60, for example, a selenium based amorphous Se film with a thickness of 10 to 1500 μm may be used. Alternatively, $PbI_2$, $HgI_2$, $Cd(Zn)Te$, $Bi_{12}TiO_{20}$, $Bi_{12}SiO_{20}$, or $Bi_{12}GeO_{20}$ may also be used. Semiconductor layer 60 is formed on active matrix substrate 70 by a vacuum deposition method or the like.

Upper electrode 50 is formed of a conductive material having a low resistance, such as Au, Al, or the like, with a thickness capable of transmitting emitted radiation. Note that intermediate layers may be provided between upper electrode 50 and semiconductor layer 60. Such intermediate layers include a charge transport layer for preventing charge injection from upper electrode 50 and allowing charges of those generated in the semiconductor layer having opposite polarity to that of injected charges to reach upper electrode 50, a crystallization prevention layer for preventing crystallization of the amorphous Se, and the like.

As illustrated in FIG. 15, active matrix substrate 70 includes glass substrate 71 on which multiple unit elements 72, which include charge collection electrodes and switch elements corresponding to pixels forming radiation image of a subject, are disposed two-dimensionally.

Figure 16:
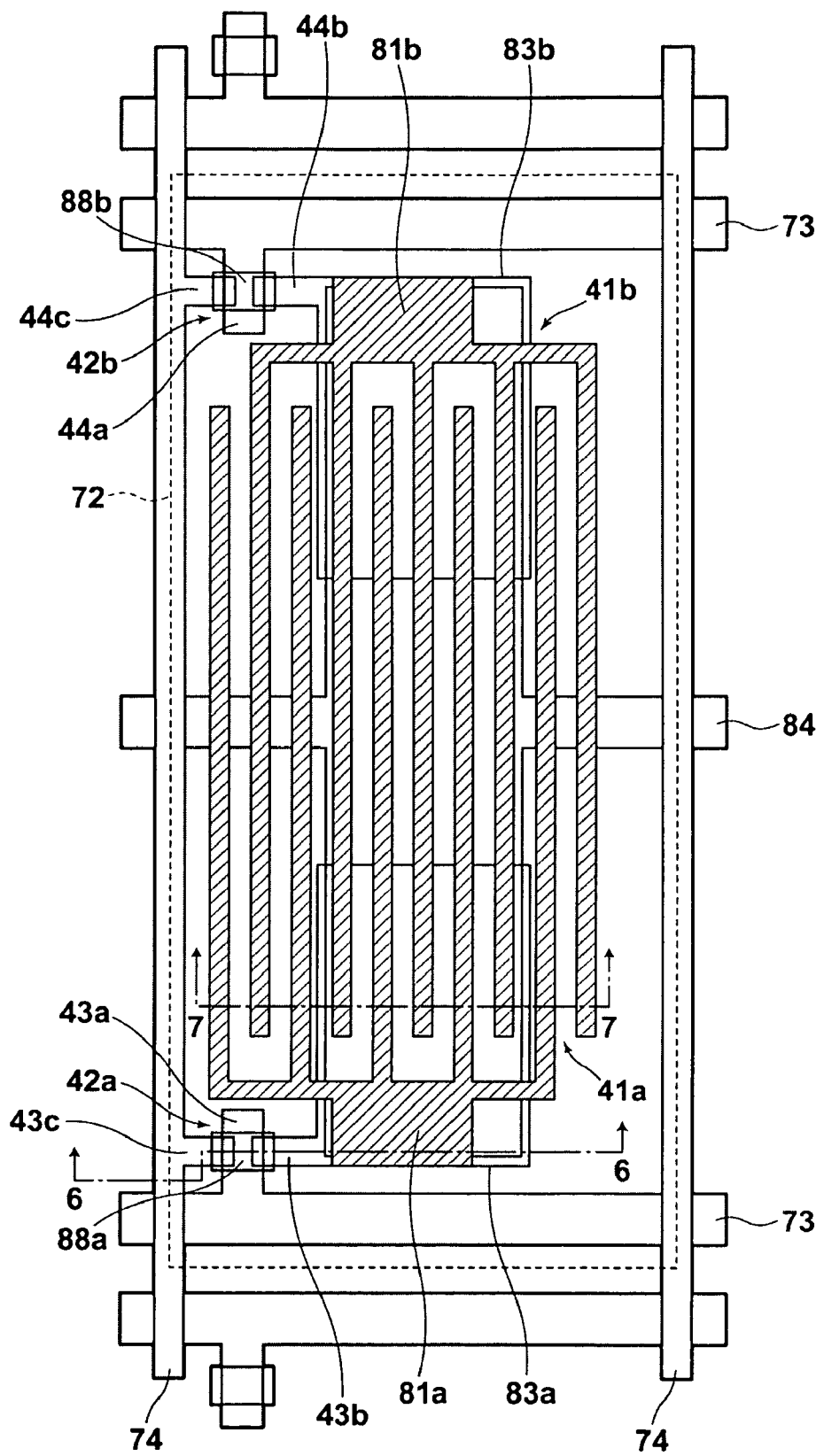
FIG. 16 is a partial plan view of the periodic information imaging radiation image detector.
Figure 17:
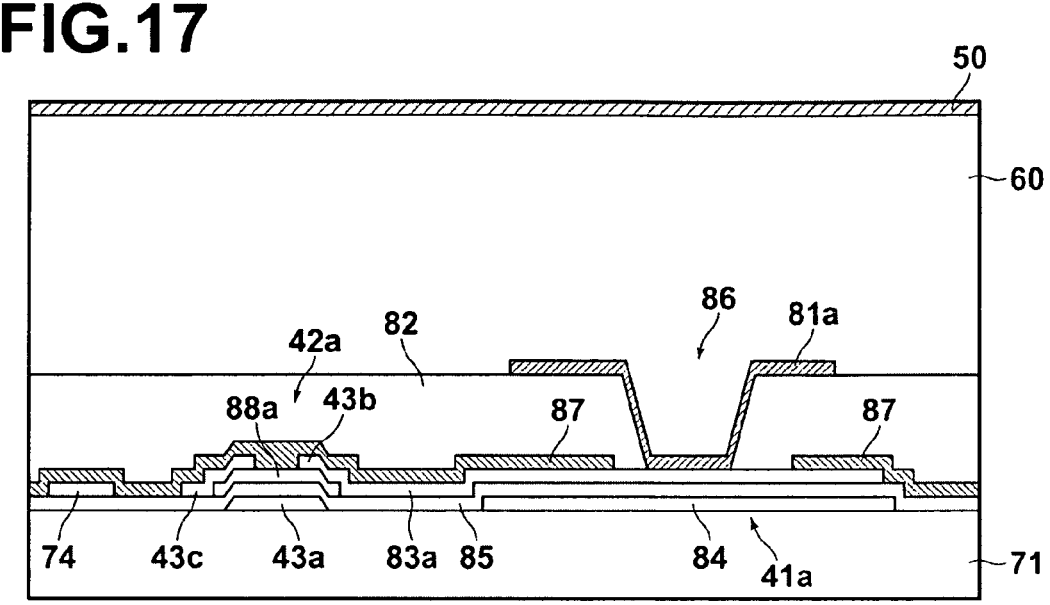
FIG. 17 is a sectional view of the partial periodic information imaging radiation image detector taken along the line 6-6 in FIG. 16.
Figure 18:
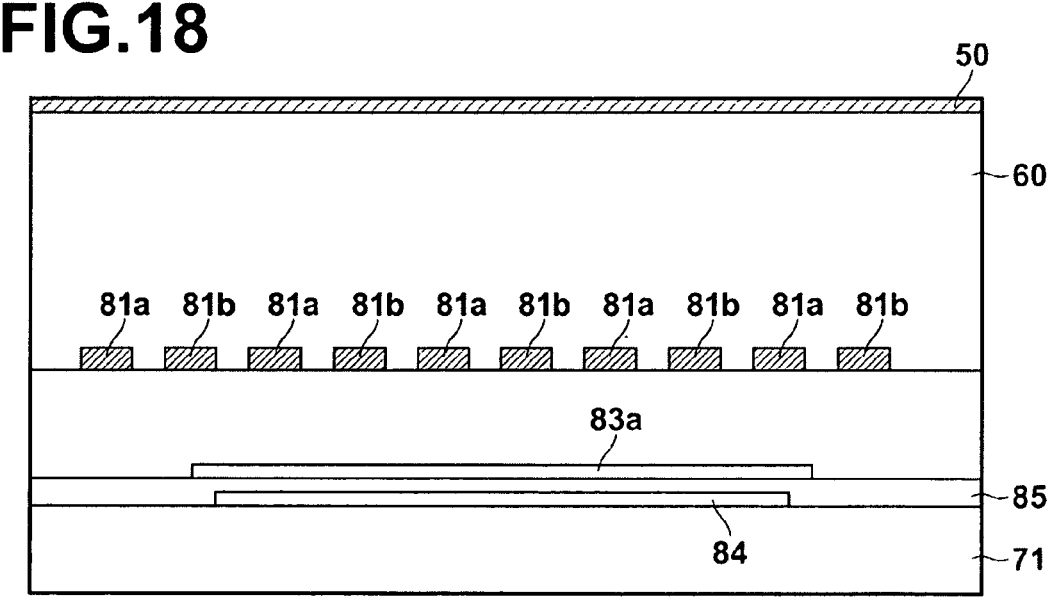
FIG. 18 is a sectional view of the partial periodic information imaging radiation image detector taken along the line 7-7 in FIG. 16.

The structure of each pixel or sub-pixel of periodic information imaging radiation image detector 40 will now be described in detail. The term "sub-pixel" as used herein refers to a pair of two linear electrode groups alternately disposed such that the phase of the arrangement period become opposite to each other. FIG. 16 is a plan view of periodic information imaging radiation image detector 40, FIG. 17 is a sectional view of periodic information imaging radiation image detector 40 taken along the line 6-6 in FIG. 16, and FIG. 18 is a sectional view of periodic information imaging radiation image detector 40 taken along the line 7-7 in FIG. 16.

Periodic information imaging radiation image detector 40 includes a charge collection electrode, constituted by first linear electrode group 81a and second linear electrode group 81b, for collecting charges generated in semiconductor layer 60, first storage capacitor 41a for storing charges collected by first linear electrode group 81a, second storage capacitor 41b for storing charges collected by second linear electrode group 81b, a first TFT switch 42a for reading out the charges stored in first storage capacitor 41a, a second TFT switch 42b for reading out the charges stored in second storage capacitor 41b.

Figure 19:
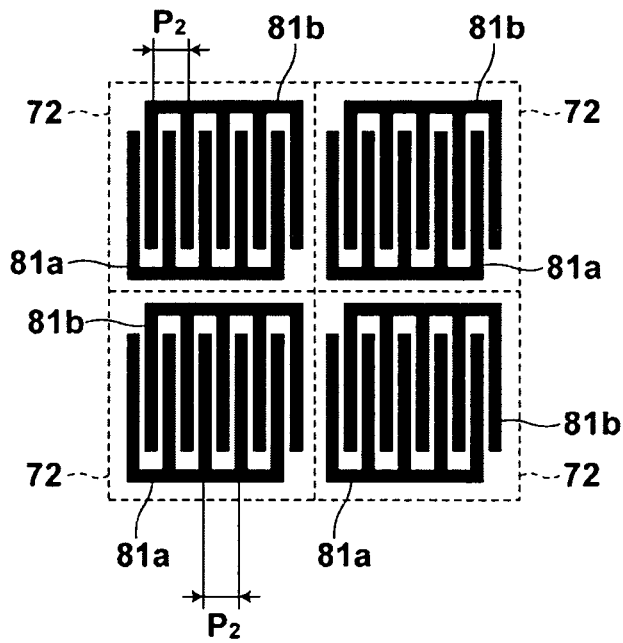
FIG. 19 is a schematic view of first linear electrode groups and second linear electrode groups of unit elements corresponding to four pixels.

FIG. 19 schematically illustrates first linear electrode groups 81a and second linear electrode groups 81b of unit elements 72 corresponding to four pixels. Each of first linear electrode group 81a and second linear electrode group 81b includes multiple linear electrodes periodically disposed with a pitch of $P_2$. A linear electrode of second linear electrode group 81b is disposed between linear electrodes of first linear electrode group 81a such that the phase of the arrangement period of linear electrodes of first linear electrode groups 81a and the phase of the arrangement period of linear electrodes of second linear electrode group 81b are shifted by n (180°=a half of the pitch) from each other. As illustrated in FIG. 19, linear electrodes of first linear electrode group 81a are connected to each other, and linear electrodes of second linear electrode group 81b are connected to each other. Preferably, the connection wire connecting the linear electrodes is provided on a different plane from that of the linear electrodes so as not to function as an electrode, but the influence of the connection wire may be substantially reduced to a negligible level by reducing the width of the connection wire.

Arrangement pitch $P_2$ of linear electrodes of first linear electrode group 81a and arrangement pitch $P_2$ of linear electrodes of second linear electrode group 81b are set to a value in the range from 2 to 15 µm. The width of each linear electrode of first linear electrode group 81a and the width of each linear electrode of second linear electrode group 81b are set to a value in the range from 1 to 14 µm.

The ratio between distance L from radiation source 1a to diffraction grating 20 and pitch $P_1$ in diffraction grating 20 may be set substantially equal to the ratio between distance from radiation source 1a to periodic information imaging radiation image detector 40, $L+Z_3$ and pitch $P_2$ of linear electrodes of periodic information imaging radiation image detector 40.

For example, first linear electrode group 81a and second linear electrode group 81b may be formed of an amorphous transparent conductive oxide film.

Note that intermediate layers may be provided between first linear electrode group 81a and second linear electrode group 81b and semiconductor layer 60. Such intermediate layers include a charge transport layer for preventing charge injection from the electrodes and allowing charges generated in semiconductor layer 60 to be collected by first linear electrode group 81a and second linear electrode group 81b, a crystallization prevention layer for preventing crystallization of the amorphous Se, and the like.

First storage capacitor 41a is constituted by connection electrode 83a, gate insulation film 85, and charge storage capacitor electrode 84, in which gate insulation film 85 acts as a dielectric body and charges are stored between connection electrode 83a and charge storage capacitor electrode 84. Second storage capacitor 41b is constituted by connection electrode 83b, gate insulation film 85, and charge storage capacitor electrode 84, in which gate insulation film 85 acts as a dielectric body and charges are stored between connection electrode 83b and charge storage capacitor electrode 84.

First TFT switch 42a is constituted by gate electrode 43a formed by extending scanning wire 73, to be described later, drain electrode 43b formed by extending connection electrode 83a, source electrode 43c formed by extending data wire 74, to be described later, gate insulation film 85, semiconductor film 88a, and the like. Second TFT switch 42b is constituted by gate electrode 44a formed by extending scanning wire 73, drain electrode 44b formed by extending connection electrode 83b, source electrode 44c formed by extending data wire 74, gate insulation film 85, semiconductor film 88b, and the like. For example, gate insulation film 85 is formed of $SiN_x$, $SiO_x$, or the like. Semiconductor films 88a, 88b are channel sections of first and second TFT switches 42a, 42b, which are current paths connecting data wire 74 to connection electrodes 83a, 83b.

Insulation protection film 87 is formed so as to cover first storage capacitor 41a and second storage capacitor 41b, first TFT switch 42a and second TFT switch 42b, data wire 74, and the like. Contact holes 86 are formed in insulation protection film 87 at a connection section between first linear electrode group 81a and connection electrode 83a, and at a connection section between second linear electrode group 81b and connection electrode 83b.

Interlayer insulation film 82 is formed on insulation protection film 87 and contact holes 86 are formed through the interlayer insulation film 82, through which first linear electrode group 81a is connected to connection electrode 83a, and second linear electrode group 81b is connected to connection electrode 83b. Interlayer insulation film 82 is an organic insulation film to electrically insulate and isolate first TFT switch 42a from second TFT switch 42b. For example, an acrylic resin may be used as the material of the organic insulation film.

As illustrated in FIG. 16, scanning wires 73 and data wires 74 are electrode wires disposed in a grid pattern, and first TFT switch 42a or second TFT switch 42b is formed adjacent to each intersection point. Different scanning wires 73 are connected to first TFT switch 42a and second TFT switch 42b, and first TFT switch 42a and second TFT switch 42b are configured to be ON/OFF controlled independently.

A readout circuit (not shown) constituted by an amplifier for detecting a signal charge flowing out to data wire 74 is connected at the end of data wire 74. A gate driver (not shown) that outputs control signals for independently controlling first TFT switch 42a and second TFT switch 42b is connected to scanning wire 73.

As described above, shifting mechanism 55 is a mechanism for shifting diffraction gratings 20 and periodic information imaging radiation image detector 40 in X direction. For example, diffraction grating 20 and periodic information imaging radiation image detector 40 may be shifted by 1/n (n is an integer not less than two) of arrangement pitch $P_2$ of the linear electrodes of periodic information imaging radiation image detector 40 to take a radiation image at each position, whereby image signals of n-types of phase components may be obtained. It is preferable, for example, to shift periodic information imaging radiation image detector 40 such that image signals corresponding to four or six types of phase components are obtained. When the charge collection electrode is formed of first linear electrode group 81a and second linear electrode group 81b, as in the present embodiment, four types of phase components may be obtained by shifting detector 40 by ½ of arrangement pitch $P_2$ and six types of phase components may be obtained by shifting detector 40 by ⅓ of arrangement pitch $P_2$. When forming a phase image with signals corresponding to two types of phase components, shifting mechanism is not required.

Next, an operation for recording a radiation image to and reading out from the periodic information imaging radiation image detector of the radiation phase image radiographing apparatus according to the present embodiment will be described First, subject 10 is placed between radiation emission unit 1 and diffraction grating 20. In the radiation phase image radiographing apparatus according to the present embodiment, subject 10 is placed between radiation emission unit 1 and diffraction grating 20, but subject 10 may be placed between diffraction grating 20 and periodic information imaging radiation image detector 40. In this case, the distance from the subject to periodic information imaging radiation image detector 40 becomes shorter and the magnification rate is reduced, which allows the apparatus to be easily installed in an existing radiography room.

Next, radiation is emitted from each radiation source 1a of radiation emission unit 1 at the same time onto diffraction grating 20. The radiation emitted on diffraction grating 20 passes through diffraction grating 20. At this time, a Talbot effect is produced in diffraction grating 20. The Talbot effect as used herein refers to that, when a plane wave passes through a phase diffraction grating, a self-image of the diffraction grating is formed at the distance given by $Z_3$ described above. In the case described above, the radiation is phase shifted by subject 10, so that the wave front of the radiation incident on diffraction grating 20 is distorted. Accordingly, the self-image of diffraction grating 20 is deformed according to the distortion.

Then, with a positive voltage being applied to upper electrode 50 of periodic information imaging radiation image detector 40 by a voltage source, the radiation representing a self-image formed by the Talbot effect of diffraction grating 20 in the manner as described above is emitted to periodic information imaging radiation image detector 40 from the side of upper electrode 50. In the radiation phase image radiographing apparatus of the present embodiment, periodic information imaging radiation image detector 40 is disposed such that upper electrode 50 is oriented to the side of radiation emission unit 1 and the length direction of each linear electrode of first and second linear electrode groups 81a and 81b corresponds to the length direction of each diffraction member 22 of diffraction grating 20.

The radiation emitted on periodic information imaging radiation image detector 40 transmits through upper electrode 50 and exposes semiconductor layer 60. Then, semiconductor layer 60 generates charge pairs by the exposure of the radiation, and negative charges of the charge pairs are combined with positive charges charged on upper electrode 50 and dissolved, while positive charges of the charge pairs are collected by first and second linear electrode groups 81a, 81b of each unit element 72, and stored in first and second storage capacitors 41a, 41b.

Figure 20:
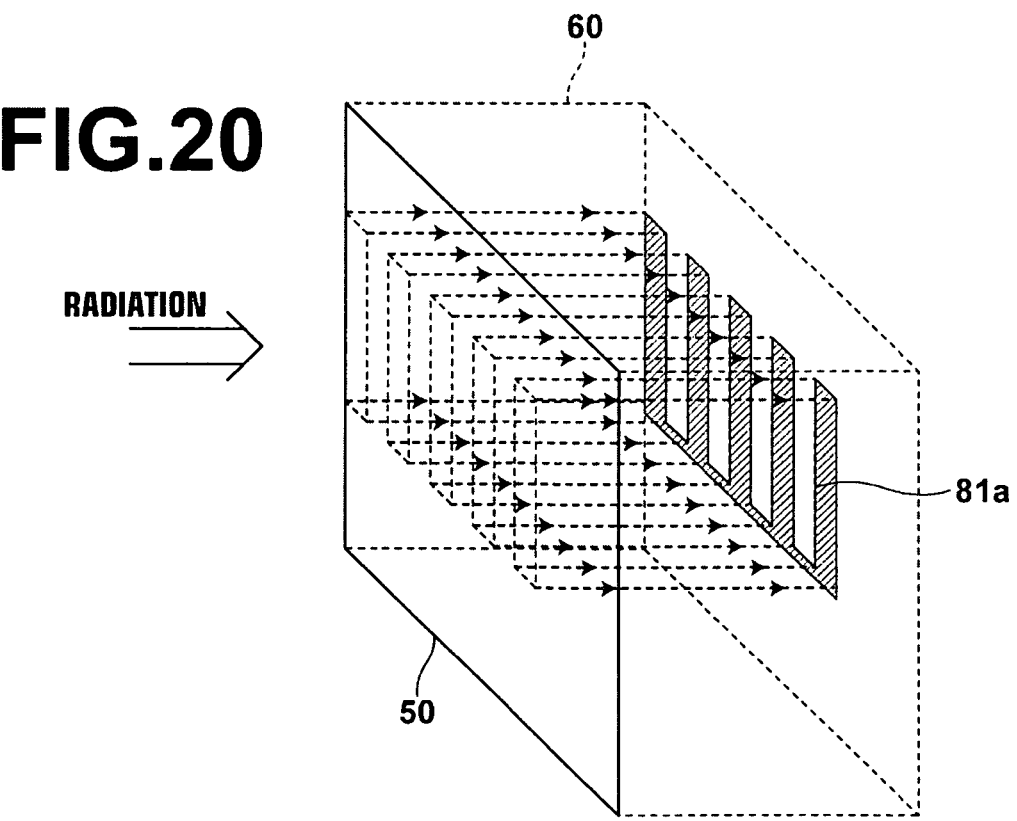
FIG. 20 illustrates an electric field formed in a semiconductor layer by the first linear electrode group.

Now, in periodic information imaging radiation image detector 40 of radiation phase image radiographing apparatus of the present embodiment, the charge collection electrode for collecting charges generated in semiconductor layer 60 is constituted by first linear electrode group 81a and second linear electrode group 81b. Therefore, when a voltage is applied to upper electrode 50 in the manner as described above, electric fields are formed in semiconductor layer 60 toward first and second linear electrode groups substantially parallel to each other, i.e., substantially perpendicular to the surface of upper electrode 50, as illustrated by dotted arrows in FIG. 20. The charges generated in semiconductor layer 60 are collected by first and second linear electrode groups 81a, 81b along the electric fields, so that first and second linear electrode groups 81a, 81b perform a function equivalent to that of the combination of an amplitude diffraction grating and a detector provided in the later stage of the grating. Accordingly, charges representing image contrast generated by the superimposition of a self-image of the deformed diffraction grating 20 and a virtual diffraction grating formed by first linear electrode group 81a are stored in first charge capacitor 41a, and charges representing image contrast generated by the superimposition of a self-image of the deformed diffraction grating 20 and a virtual diffraction grating formed by second linear electrode group 81b are stored in second charge capacitor 41b. The image contrast described above generally takes the form of Moire fringes. As described above, first linear electrode group 81a and second linear electrode group 81b are phase shifted by n from each other, thus signals corresponding to two types of phase components phase shifted from each other by n are detected by periodic information imaging radiation image detector 40.

Then, control signals for turning ON first TFT switches 42a are sequentially outputted from the not shown gate driver to each scanning wire 73 connected to first TFT switches 42a. Then, first TFT switches 42a are turned ON according to the control signals outputted from the gate driver, and charges stored in first storage capacitor 41a of each unit element 72 are read out to data wire 74. The charge signal flowed out to data wire 74 is detected by the charge amplifier of a not shown readout circuit as an image signal corresponding to a first phase component.

Then, control signals for turning ON second TFT switches 42b are sequentially outputted from the not shown gate driver to each scanning wire 73 connected to second TFT switches 42b. Then, second TFT switches 42b are turned ON according to the control signals outputted from the gate driver, and charges stored in second storage capacitor 41b of each unit element 72 are read out to data wire 74. The charge signal flowed out to data wire 74 is detected by the charge amplifier of a not shown readout circuit as an image signal corresponding to a second phase component.

Thereafter, periodic information imaging radiation image detector 40 is shifted by shifting mechanism 55, and the image recording in the detector 40 and image signal reading from the detector 40 are performed at each predetermined position, whereby image signals corresponding to the first and second phase components are detected at each predetermined position.

Image signals detected in the manner as described above are inputted to phase image acquisition unit 6. Then, phase image acquisition unit 6 generates a partial phase image with respect to each detection area of periodic information imaging radiation image detector 40 based on image signals of a plurality of phase components detected by periodic information imaging radiation image detector 40 in each detection area corresponding to the irradiation range of radiation emitted from each radiation source 1*a*. That is, a partial phase image corresponding to each radiation source 1*a* is generated. Thereafter, the partial phase images are combined to produce a complete phase image.

Next, a modification of periodic information imaging radiation image detector 40 of radiation phase image radiographing apparatus according to the second embodiment will be described.

Figure 21:
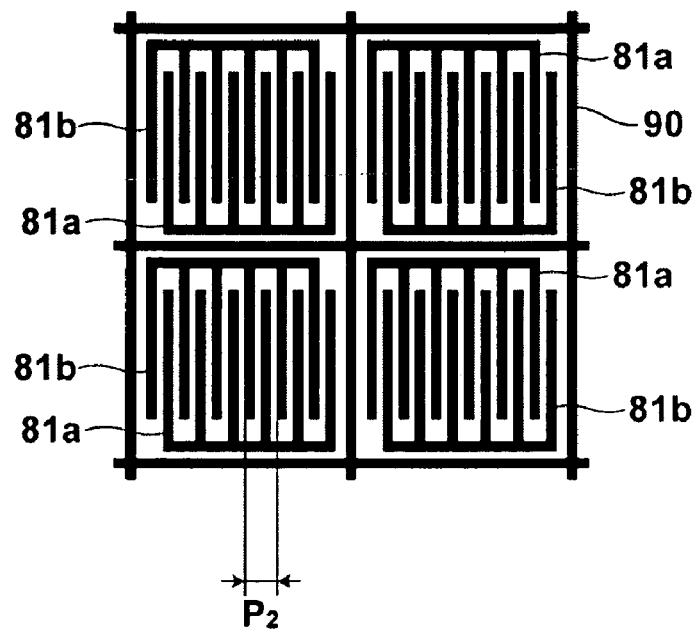
FIG. 21 illustrates a modification of the periodic information imaging radiation image detector in the radiation phase image radiographing apparatus according to the second embodiment.

In addition to first linear electrode group 81*a* and second linear electrode group 81*b* of periodic information imaging radiation image detector 40 shown in FIG. 19, constant potential linear electrode 90 may be provided in a grid pattern enclosing the charge collection electrode, constituted by first and second linear electrode groups 81*a*, 81*b*, of each unit element 72, as illustrated in FIG. 21. If a gap is present between charge collection electrodes, electric fields are bent and a charge is collected from a portion where the linear electrode is not present, whereby phase component contamination occurs. Consequently, the provision of constant potential linear electrode 90 to which a constant potential is applied allows stabilization of the electric fields and prevention of the contamination described above. A potential that does not cause a large potential difference with an adjacent charge collection electrode is applied to constant potential linear electrode 90. That is, substantially the same potential as that of the charge collection electrode is applied. More specifically, constant potential linear electrode 90 is set to a ground potential or a value close to the ground potential. Where constant potential linear electrode 90 is provided, it is preferable to arrange and dispose first linear electrode group 81*a* and second linear electrode group 81*b* in the manner shown in FIG. 21.

In periodic information imaging radiation image detector 40 of the present embodiment, first linear electrode group 81*a* and second linear electrode group 81*b*, phase shifted by n from each other, are provided in each unit element 72 as the charge collection electrode. The shape of the charge collection electrode is not limited to this.

Figure 22:
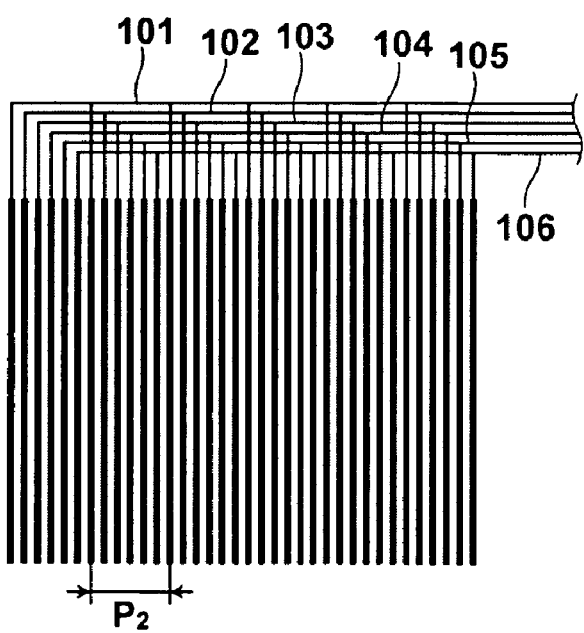
FIG. 22 illustrates a modification of the periodic information imaging radiation image detector in the radiation phase image radiographing apparatus according to the second embodiment.

For example, first to sixth linear electrode groups 101 to 106, each having multiple linear electrodes arranged with pitch P$_2$, may be disposed such that the phase of the arrangement period of linear electrodes of each linear electrode group is shifted by π/3 from each other, as illustrated in FIG. 22. More specifically, first to sixth linear electrode groups 101 to 106 may be disposed such that, when the phase of first linear electrode group 101 is 0, the phase of second linear electrode group 102 is π/3, the phase of third linear electrode group 103 is 2π/3, the phase of fourth linear electrode group 104 is n, the phase of fifth linear electrode group 105 is 4π/3, and the phase of sixth linear electrode group 106 is 5π/3.

Formation of the charge collection electrode in the manner illustrated in FIG. 22 to read out charges collected by first to sixth linear electrode groups 101 to 106 with respect to each linear electrode group allows acquisition of image signals corresponding to six types of phase components having different phases by one radiographing operation. Accordingly, shifting mechanism 55 is not required.

Figure 23:
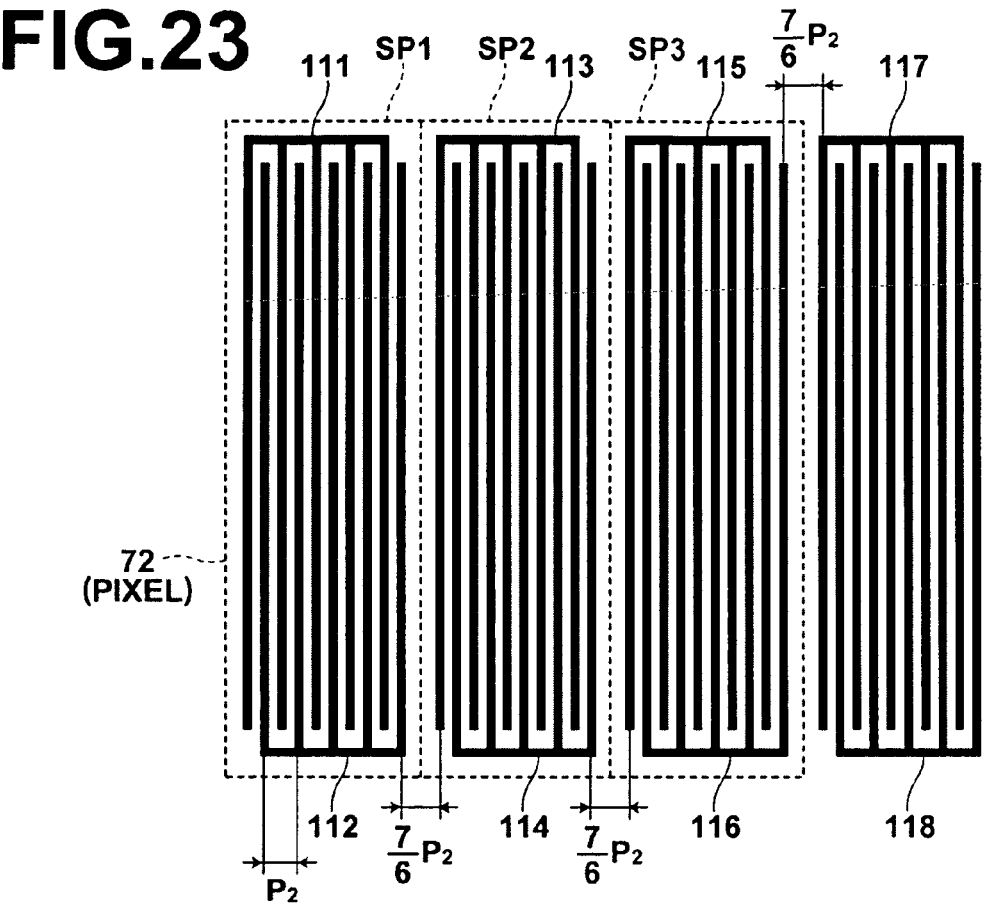
FIG. 23 illustrates a modification of the periodic information imaging radiation image detector in the radiation phase image radiographing apparatus according to the second embodiment.

Further, as illustrated in FIG. 23, a pixel corresponding to one unit element 72 may be divided into a plurality of sub-pixels (here, three sub-pixels) and linear electrode groups having different phases may be disposed in each sub-pixel. In the present embodiment, the sub-pixel refers to a pair of two linear electrode groups alternately disposed such that the phase of the arrangement period becomes opposite to each other.

More specifically, in the modification shown in FIG. 23, first linear electrode group 111 in which linear electrodes are arranged with pitch P$_2$ and second linear electrode group 112 in which linear electrodes are arranged with pitch P$_2$ are disposed in sub-pixel SP1 so as to have a phase difference of n from each other, third linear electrode group 113 in which linear electrodes are arranged with pitch P$_2$ and fourth linear electrode group 114 in which linear electrodes are arranged with pitch P$_2$ are disposed in sub-pixel SP2 so as to have a phase difference of n from each other, and fifth linear electrode group 115 in which linear electrodes are arranged with pitch P$_2$ and sixth linear electrode group 116 in which linear electrodes are arranged with pitch P$_2$ are disposed in sub-pixel SP3 so as to have a phase difference of n from each other. Then, adjacent linear electrode groups of sub-pixel SP1 and sub-pixel SP2 are disposed at a distance of (⅞)×pitch P$_2$, and adjacent linear electrode groups of sub-pixel SP2 and sub-pixel SP3 are disposed at a distance of (⅞)×pitch P$_2$, whereby the phase is shifted by 4π/3 between sub-pixels. Arrangement of the linear electrode groups in one pixel in the manner shown in FIG. 23 results in that, when the phase of first linear electrode group 111 is 0, the phase of second linear electrode group 112 is n, the phase of third linear electrode group 113 is 4π/3, the phase of fourth linear electrode group 114 is π/3, the phase of fifth linear electrode group 115 is 2π/3, and the phase of sixth linear electrode group 116 is 5π/3. Note that linear electrode group 117 and linear electrode group 118 are the linear electrode groups of adjacent pixel.

Formation of the charge collection electrode in the manner illustrated in FIG. 22 to read out charges collected by first to sixth linear electrode groups 111 to 116 with respect to each linear electrode group allows acquisition of image signals corresponding to six types of phase components by one radiographing operation. The structure of charge collection electrode shown in FIG. 22 also allows acquisition of image signals corresponding to six types of phase components by one radiographing operation, but the structure of charge collection electrode shown in FIG. 23 allows the use of wider linear electrodes in comparison with the structure of FIG. 22. The spatial resolution is somewhat degraded in the structure shown in FIG. 22, but the structure allows easy connection of linear electrodes.

As described above, it is preferable that each radiation sources 1*a* emits radiation such that the exposure area at the position of subject 10 is arranged without any space and at an angle that substantially does not influence the diffraction properties of diffraction grating 20 and periodic information imaging radiation image detector 40 at peripheral portions of exposure areas at the positions of diffraction grating 20 and periodic information imaging radiation image detector 40. Hereinafter, the angle will be discussed. Here, the allowable range of the angle will be discussed in terms of the positional displacement of a linear electrode group of periodic information imaging radiation image detector 40.

Figure 24:
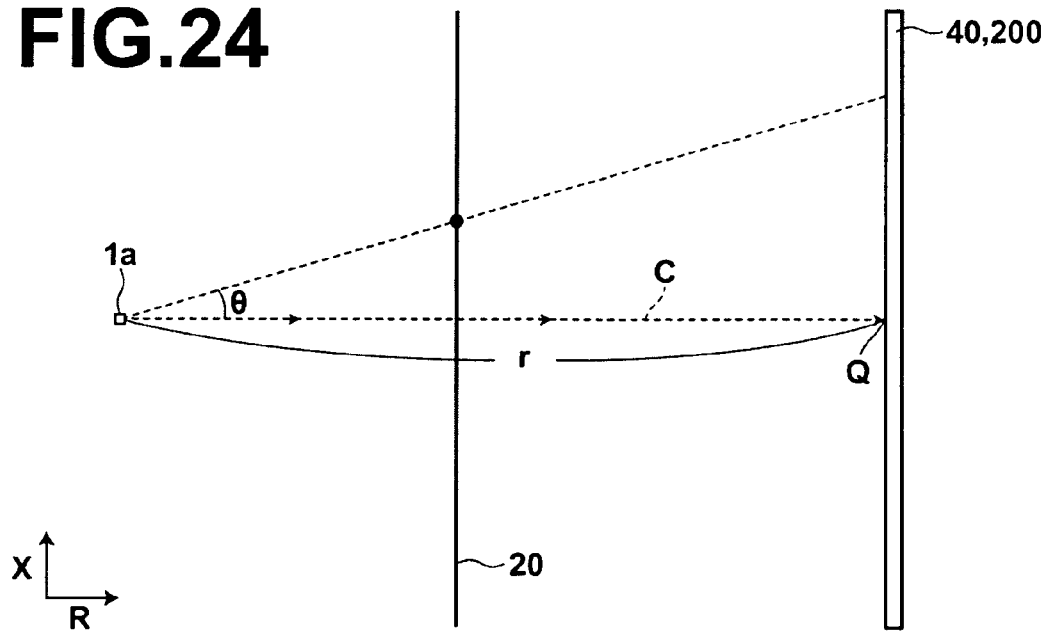
FIG. 24 illustrates conditions of spread angle of radiation emitted from a radiation source.

Assuming a required pitch of diffraction members at a position (r, x) away from intersection point Q between central axis C of radiation emitted from radiation source 1*a* and periodic information imaging radiation image detector 40 by distance x in a direction orthogonal to the diffraction members to be Δx, Δx can be represented by Formula (10) below (FIG. 24, which is a top view of the radiation phase image radiographing apparatus shown in FIG. 13. The thickness direction in FIG. 24 corresponds to Y direction in FIG. 13.)

$$\Delta x = r\Delta\theta \times \frac{\tan\theta}{\theta} \times \left\{ \sqrt{(r^2 + x^2)} \times \frac{1}{r} \right\} \times \frac{1}{\cos\theta} \quad (10)$$

where, r is the distance from radiation source 1*a* (if a slit is used in the radiation emission unit, to be described later, from the position of the slit) to periodic information imaging radiation image detector 40, and $r\Delta\theta$ is the pitch of the linear electrodes at intersection point Q between the central axis C of the radiation beam and periodic information imaging radiation image detector 40.

Here, $x/r = \tan\theta$, which is substituted to Formula (10) above, then $\Delta x$ can be represented by Formula (11) below.

$$\Delta x = r\Delta\theta \times \frac{\tan\theta}{\theta} \times \frac{\sqrt{1 + \tan^2\theta}}{\cos\theta} = r\Delta\theta \times \frac{\tan\theta}{\theta\cos^2\theta} \quad (11)$$

Thus, the ratio between the pitch at (r, x) and the pitch $r\Delta\theta$ at intersection point Q can be represented by Formula (12) below.

$$\frac{\Delta x}{r\Delta\theta} = \frac{\tan\theta}{\theta\cos^2\theta} \quad (12)$$

Relationship between $\theta$ and $\Delta x/r\Delta\theta$ obtained based on Formula (12) above is summarized in Table 2 below.

TABLE 2

| | $\theta$ | | | | |
|---|---|---|---|---|---|
| | 1.0° | 2.0° | 5.0° | 10.0° | 15.0° |
| $\Delta x/r\Delta\theta$ | 1.0004 | 1.002 | 1.01 | 1.04 | 1.10 |

Here, assuming that charge collection electrodes of periodic information imaging radiation image detector 40 are structured in the manner shown in FIG. 23, with pitch $P_2$ of the linear electrodes to be 0.8 μm and a line width of the linear electrode to be 3 μm, the width of linear electrode group for detecting a signal corresponding to one phase component is 35 μm and one pixel has a width of about 120 μm.

If the phase of each linear electrode group is shifted about $\frac{1}{12}$ of the pitch, it is thought to be undesirable that a signal of different phase component is mixed in the same pixel. Given that the radiation beam spreads from the central axis to X direction (direction orthogonal to the diffraction members), it is preferable that the positional displacement of linear electrodes within one pixel is limited to $\frac{8}{12} \times \frac{1}{2} = \frac{8}{24} = 0.333$ μm or less.

If the pitch of the linear electrodes on central axis C is 8 μm, the distance between the centers of linear electrodes at each end of linear electrode groups in a peripheral portion of the radiation beam is $\Delta x/r\Delta\theta \times 8 \times 4$.

Accordingly, if $\Delta x/r\Delta\theta \times 8 \times 4 - 32 < 0.333$, the condition described above is met.

Thus, $\Delta x/r\Delta\theta < 1.010$.

Accordingly, it is known from Table 2 above that one-side spread angle $\theta$ of the radiation beam in X direction needs to be limited to 5° or less.

For example, if r=1000 mm, $2 \times 1000 \times \tan 5° = 175$ mm, thus the width of radiation beam emitted from one radiation source 1*a* in X direction on periodic information imaging radiation image detector 40 needs to be limited to 175 mm or less.

So far, the description has been made of a case in which the charge collection electrode is divided into three sub-pixels as shown in FIG. 23. Now, the discussion will be made of a case in which the charge collection electrode is divided into two sub-pixels and two linear electrode groups are disposed in each sub-pixel so as to have a phase difference of π from each other. Here, it is assumed that each linear electrode group has five linear electrodes, and the pitch and width of the linear electrodes are identical to those described above.

In this case, if the phase of each linear electrode group is shifted about $\frac{1}{8}$ of the pitch, it is thought to be undesirable that a signal of different phase component is mixed in the same pixel. Given that the radiation beam spreads from the central axis to X direction (direction orthogonal to the linear electrodes), it is preferable that the positional displacement of linear electrodes in one pixel is limited to $\frac{8}{8} \times \frac{1}{2} = \frac{8}{16} = 0.5$ μm or less.

If the pitch on central axis C is assumed to be 8 μm, the distance between the centers of linear electrodes at each end of linear electrode groups in a peripheral portion of the radiation beam is $\Delta x/r\Delta\theta \times 8 \times 4$.

Accordingly, if $\Delta x/r\Delta\theta \times 8 \times 4 - 32 < 0.5$, the condition described above is met.

Thus, $\Delta x/r\Delta\theta < 1.016$.

Accordingly, it is known from Table 2 above that one-side spread angle $\theta$ of the radiation beam in X direction needs to be limited to 6° or less.

For example, if r=1000 mm, $2 \times 1000 \times \tan 6° = 210$ mm, thus the width of radiation beam emitted from one radiation source 1*a* in X direction on periodic information imaging radiation image detector 40 needs to be limited to 210 mm or less.

The above discussion shows that the pitch of the linear electrodes is not restricted by spread angle $\theta$ of the radiation beam.

Figure 25:
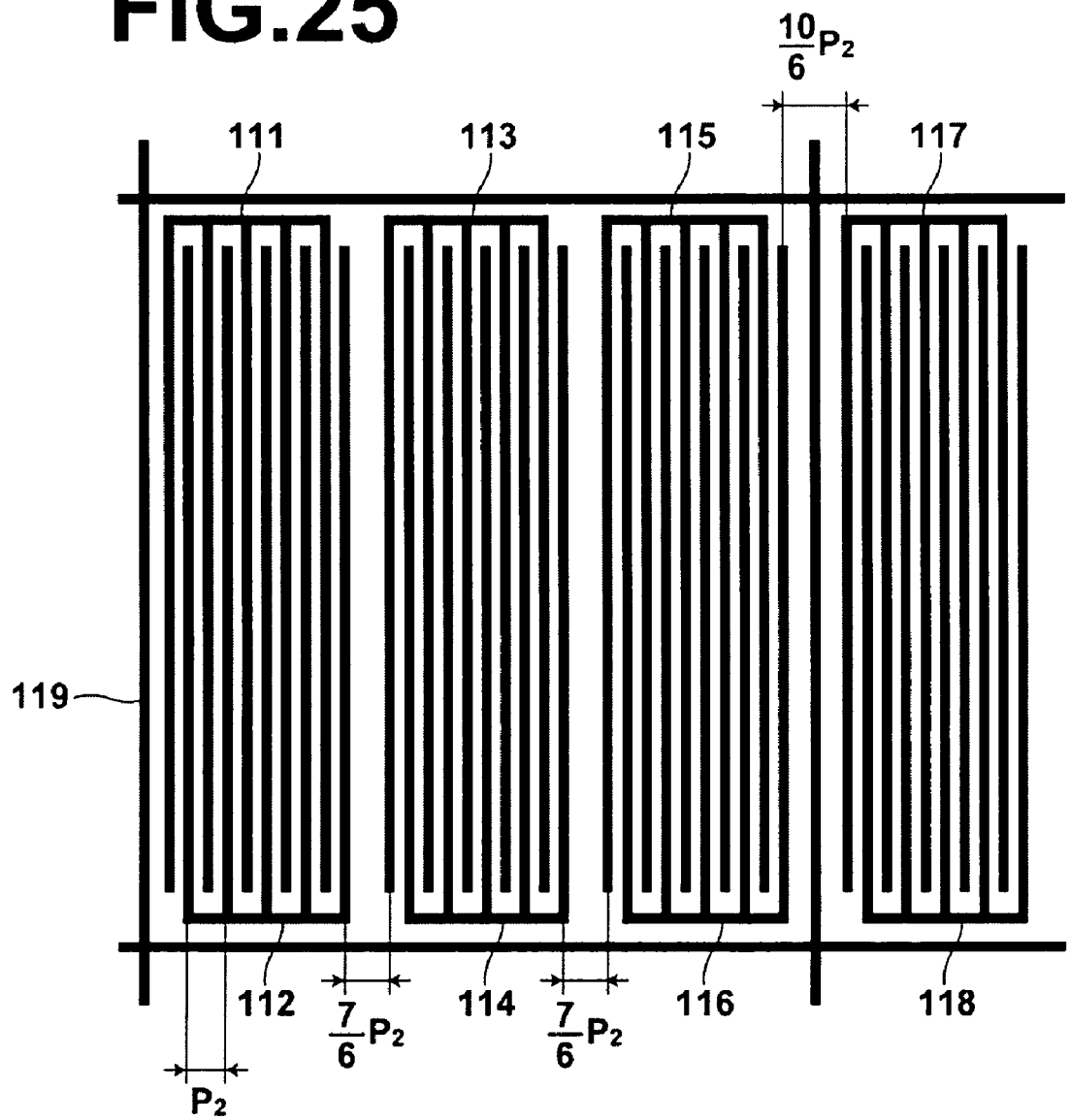
FIG. 25 illustrates a modification of the periodic information imaging radiation image detector in the radiation phase image radiographing apparatus according to the second embodiment.

In addition to first to sixth linear electrode groups 111 to 116 shown in FIG. 23, constant potential electrode 119 may be provided in a grid pattern enclosing the charge collection electrode, constituted by first to sixth linear electrodes 111 to 116, of each unit element 72, as illustrated in FIG. 25. The effect of the constant potential electrode 119 is identical to that described in relation to FIG. 21. A potential that does not cause a large potential difference with an adjacent charge collection electrode is applied to constant potential electrode 119. That is, substantially the same potential as that of the charge collection electrode is applied. More specifically, constant potential electrode 119 is set to a ground potential or a value close to the ground potential. Where constant potential electrode 119 is provided, the pitch between linear electrode groups of adjacent pixels in a direction orthogonal to the linear electrodes, i.e., between linear electrode group 116 and linear electrode group 117, is set to $(1\%) \times P_2$, as shown in FIG. 25.

Figure 26:
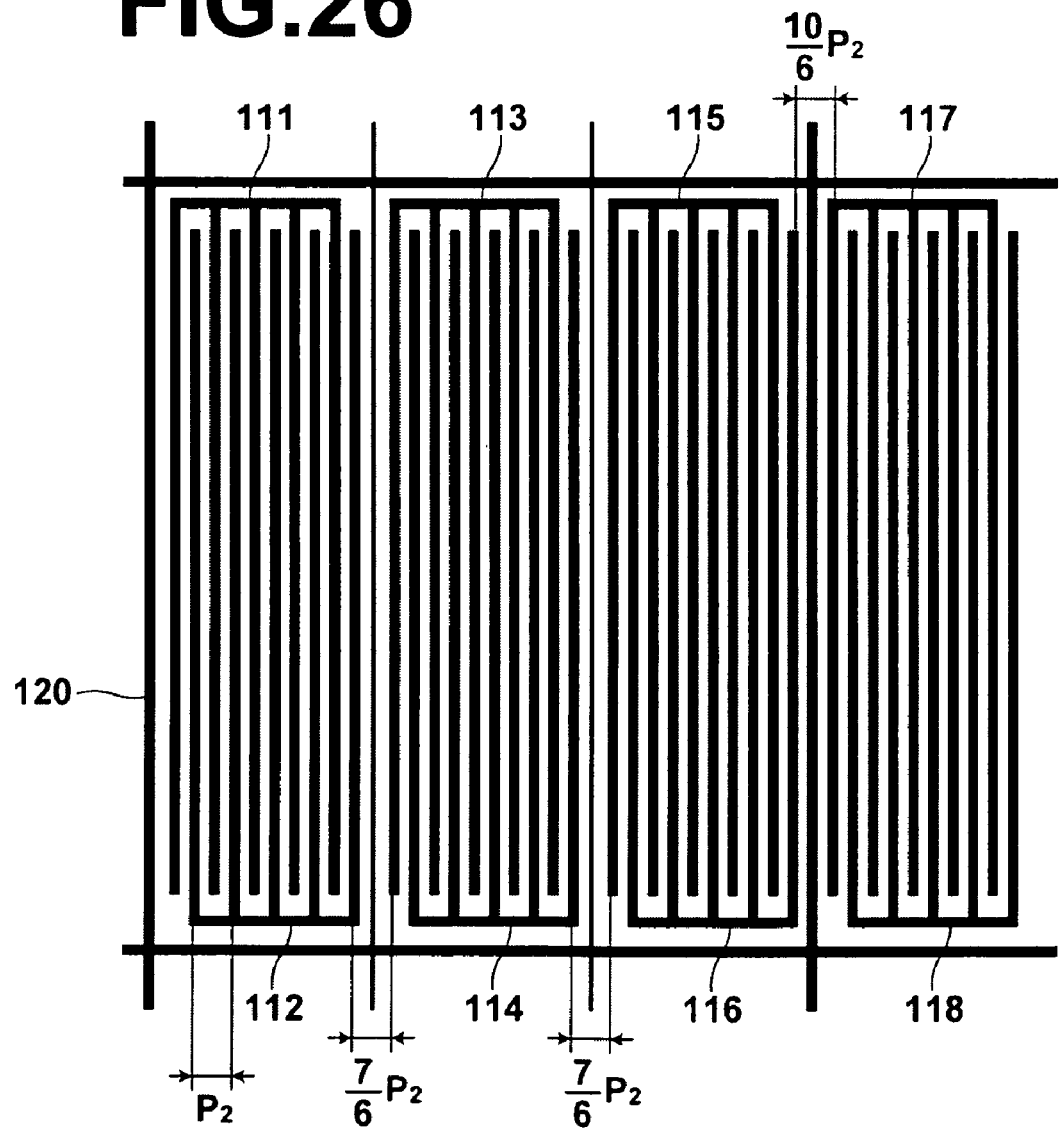
FIG. 26 illustrates a modification of the periodic information imaging radiation image detector in the radiation phase image radiographing apparatus according to the second embodiment.

Instead of providing constant potential electrode 119 to enclose each pixel, as shown in FIG. 25, constant potential electrode 120 may be provided to enclose each sub-pixel, as shown in FIG. 26.

Figure 27:
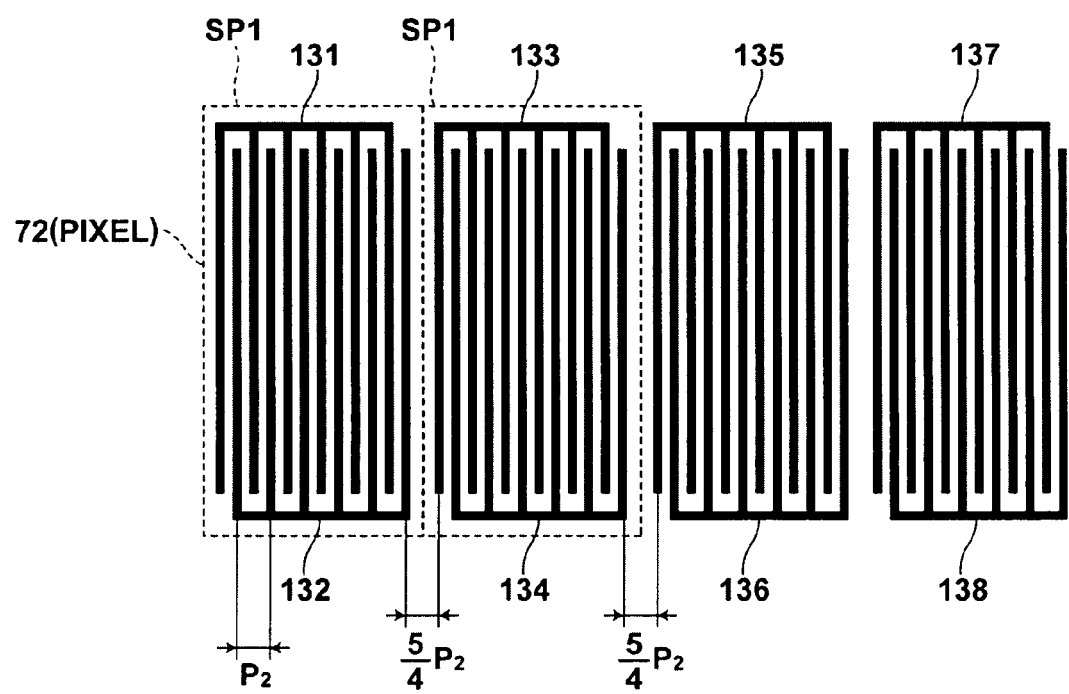
FIG. 27 illustrates a modification of the periodic information imaging radiation image detector in the radiation phase image radiographing apparatus according to the second embodiment.

Further, as illustrated in FIG. 27, a pixel corresponding to one unit element 72 may be divided into two sub-pixels, and linear electrode groups having different phases may be disposed in each sub-pixel. More specifically, in the modification shown in FIG. 27, first linear electrode group 131 in which linear electrodes are arranged with pitch $P_2$ and second linear electrode group 132 in which linear electrodes are arranged with pitch $P_2$ are disposed in sub-pixel SP1 so as to have a phase difference of π from each other, third linear electrode group 133 in which linear electrodes are arranged with pitch $P_2$ and fourth linear electrode group 134 in which linear electrodes are arranged with pitch $P_2$ are disposed in sub-pixel SP2 so as to have a phase difference of n from each other. Then, adjacent linear electrode groups of sub-pixel SP1 and sub-pixel SP2 are disposed at a distance of $(5/4) \times$pitch $P_2$. This arrangement results in that, when the phase of first linear electrode group 131 is 0, the phase of second linear electrode group 132 is n, the phase of third linear electrode group 133 is $3\pi/2$, the phase of fourth linear electrode group 134 is $\pi/2$, that is, first to fourth linear electrode groups correspond to the phases shifted by $\pi/2$ from each other. Linear electrode groups 135 to 138 are linear electrode groups of adjacent pixel. Linear electrode group 135 detects a signal having the same phase as that of first linear electrode group 131, linear electrode group 136 detects a signal having the same phase as that of second linear electrode group 132, linear electrode group 137 detects a signal having the same phase as that of third linear electrode group 133, and linear electrode group 138 detects a signal having the same phase as that of fourth linear electrode group 134.

Formation of the charge collection electrode in the manner illustrated in FIG. 27 to read out charges collected by first to fourth linear electrode groups 131 to 134 with respect to each linear electrode group allows acquisition of image signals corresponding to four types of phase components by one radiographing operation.

FIG. 23 or 27 illustrates a case where a pixel corresponding to one unit element 72 is divided into three or two sub-pixels, but the pixel may be divided into n (n>4) sub-pixels. In this case, if the pitch between adjacent linear electrode groups of adjacent sub-pixels is set to $(2n+1)P_2/2n$, linear electrode groups corresponding to phases shifted by $\pi/n$ from each other may be provided.

When a pixel is divided into two to three sub-pixels, data of four to six phase components may be obtained by one radiographing operation, and a preferable phase image may be formed. When obtaining data of four to six phase components without dividing a pixel into sub-pixels, the structure shown in FIG. 22 may be used, but each linear electrode has a narrow width, which may cause a manufacturing problem. On the other hand, n>4 while maintaining the pixel size causes each linear electrode group to have a less number of linear electrodes, whereby the accuracy as the data of phase components is degraded.

When diving a pixel into a plurality of sub-pixels in the manner as described above, it is preferable to set the width of the pair of linear electrode groups in the length direction of the linear electrodes in each sub-pixel greater than the width of the pair of linear electrode groups in a direction orthogonal to the length direction of the linear electrodes, as illustrated in FIGS. 23, and 25 to 27.

Figure 28:
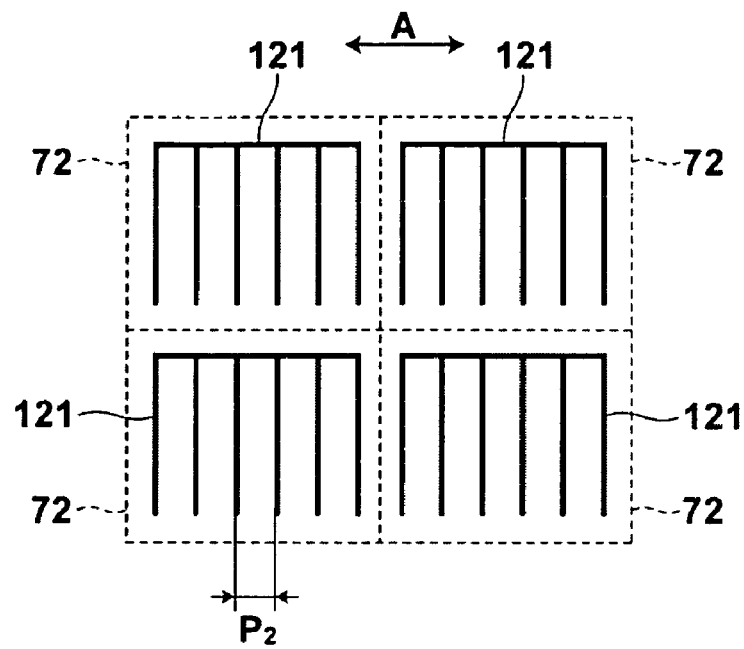
FIG. 28 illustrates a modification of the periodic information imaging radiation image detector in the radiation phase image radiographing apparatus according to the second embodiment.

The modification described above is an example in which a plurality of linear electrode groups is provided in each unit element 72. But, for example, only one linear electrode group 121, in which linear electrodes are arranged with pitch $P_2$, may be provided in each unit element 72, as illustrated in FIG. 28. FIG. 28 illustrates linear electrode groups 121 of four adjacent unit elements 72. As illustrated in FIG. 28, where the charge collection electrode of unit element 72 is formed of one linear electrode group and image signals corresponding to a plurality of types of phase components having different phases are obtained, a shifting mechanism for shifting periodic information imaging radiation image detector 40 and diffraction grating 20 in a direction orthogonal to linear electrodes (A direction in FIG. 28) along the respective planes may be provided and radiation image taking may be performed a plurality of times by shifting detector 40 and grating 20. For example, image signals corresponding to three types of phase components may be obtained by shifting detector 40 and grating 20 by $\frac{1}{3}$ of pitch $P_2$ and taking a radiation image at each position. Otherwise, image signals corresponding to six types of phase components may be obtained by shifting detector 40 and grating 20 by $\frac{1}{6}$ of pitch $P_2$ and taking a radiation image at each position.

Figure 29:
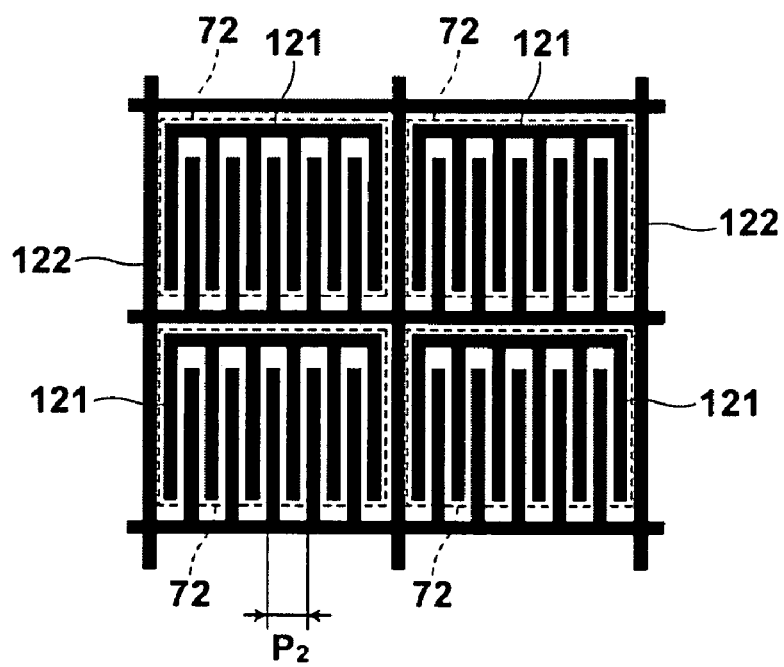
FIG. 29 illustrates a modification of the periodic information imaging radiation image detector in the radiation phase image radiographing apparatus according to the second embodiment.

In addition to the charge collection electrodes of linear electrode groups 121 shown in FIG. 28, constant potential electrode 122 may be provided as illustrated in FIG. 29. Constant potential electrode 122 is arranged so as to be disposed between each linear electrode of each linear electrode group 121 and in a grid pattern to enclose each unit element 72. The effect of the constant potential electrode 122 is identical to that described in relation to FIG. 21. A potential that does not cause a large potential difference with an adjacent charge collection electrode is applied to constant potential electrode 122. That is, substantially the same potential as that of the charge collection electrode is applied. More specifically, constant potential electrode 122 is set to a ground potential or a value close to the ground potential.

In FIG. 19, the description has been made of a case in which first linear electrode group 81$a$ and second linear electrode group 81$b$ are phase shifted by n from each other, but instead, three linear electrode groups phase shifted by $2\pi/3$ from each other may be provided in each unit element 72. If the charge collection electrode of each unit element 72 is formed of three linear electrode groups in the manner as described above and periodic information imaging radiation image detector 40 and diffraction grating 20 are shifted, for example, by $\frac{1}{2}$ of pitch $P_2$ to take a radiation image at each position, image signals corresponding to six types of phase components may be obtained.

In the radiation phase image radiographing apparatus according to the second embodiment, a radiation image detector having TFT switches is used, but a CMOS or a CCD may also be used as the switch element.

Further, in the radiation phase image radiographing apparatus according to the second embodiment, periodic information imaging radiation image detector 40 to which a positive voltage is applied when recording a radiation image is used. Alternatively, a TFT readout type radiation image detector to which a negative voltage is applied when recording a radiation image may be used.

Figure 30A:
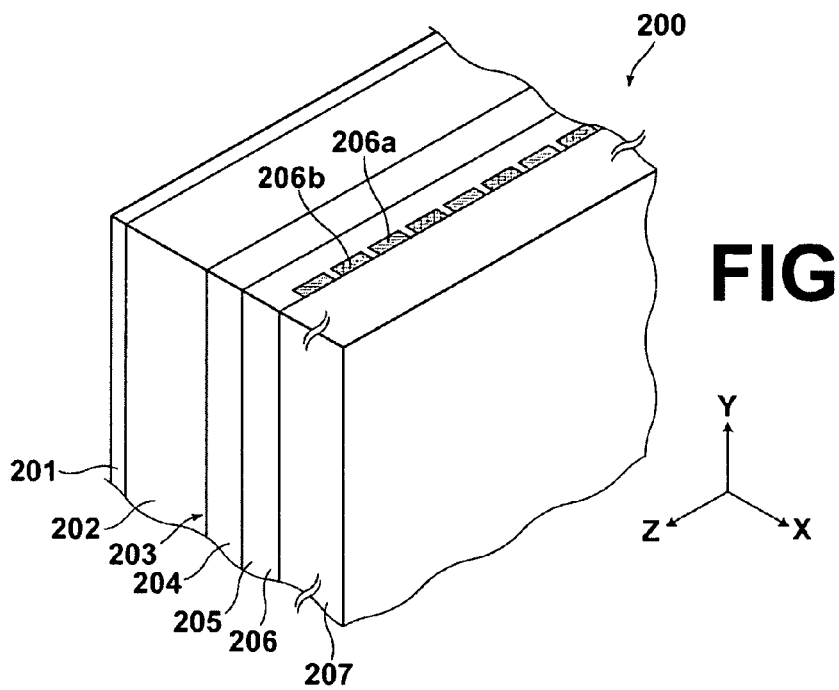
FIG. 30A is a sectional view of a periodic information imaging radiation image detector in a third embodiment of the radiation phase image radiographing apparatus of the present invention.

Next, a third embodiment of the radiation phase image radiographing apparatus of the present invention will be described. The radiation phase image radiographing apparatus according to the third embodiment uses an optical readout type periodic information imaging radiation image detector, instead of the TFT readout type periodic information imaging radiation image detector of the radiation phase image radiographing apparatus according to the second embodiment. The radiation phase image radiographing apparatus according to the third embodiment differs from the radiation phase image radiographing apparatus according to the second embodiment only in the structure of the periodic information imaging radiation image detector. Accordingly, only the structure of the periodic information imaging radiation image detector will be described. FIG. 30A is a perspective view of the periodic information imaging radiation image detector, FIG. 30B is an XZ sectional view of the periodic information imaging radiation image detector shown in FIG. 30A, and FIG. 30C is an XY sectional view of the periodic information imaging radiation image detector shown in FIG. 30A.

Figure 30B:
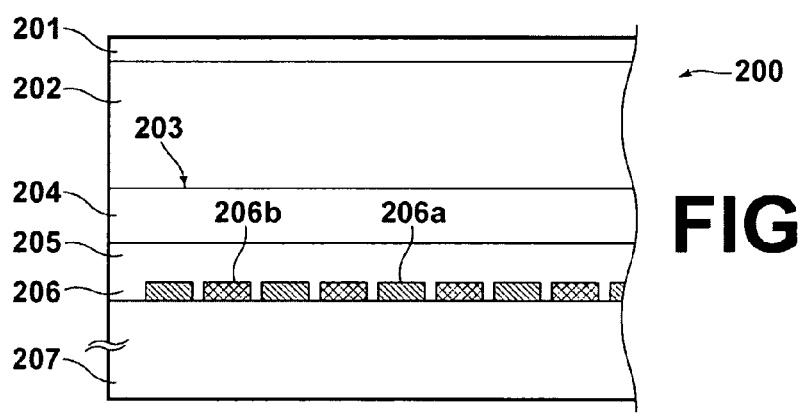
FIG. 30B is an XZ sectional view of the periodic information imaging radiation image detector shown in FIG. 30A.
Figure 30C:
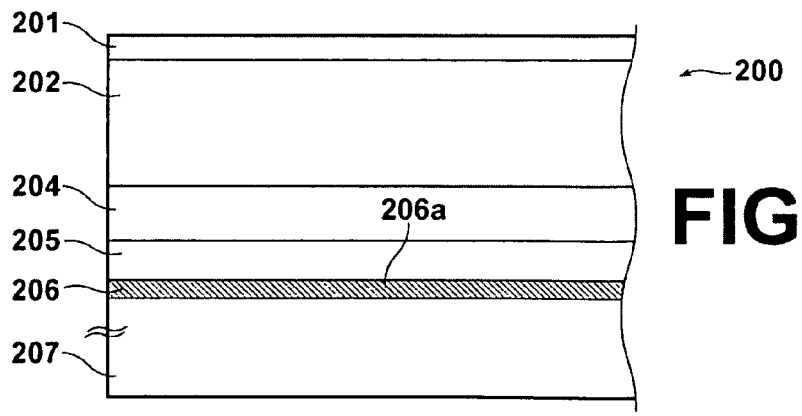
FIG. 30C is an XY sectional view of the periodic information imaging radiation image detector shown in FIG. 30A.

As illustrated in FIGS. 30A to 30C, periodic information imaging radiation image detector 200 of the radiation phase image radiographing apparatus according to the third embodiment includes the following stacked in the order listed below: first electrode layer 201 that transmits radiation; recording photoconductive layer 202 that generates charges by receiving radiation transmitted through first electrode layer 201; charge transport layer 204 that acts as an insulator against charges of one polarity of those generated in recording photoconductive layer 202 and as a conductor for charges of the other polarity; readout photoconductive layer 205 that generates charges by receiving readout light; and second electrode layer 206. Storage section 203 for storing charges generated in recording photoconductive layer 202 is formed adjacent to the interface between recording photoconductive layer 202 and charge transport layer 204. Each of the layers described above is stacked on glass substrate 207 one after another from second electrode layer 206.

First electrode layer 201 may be made of any material as long as it transmits radiation. For example, a NESA film ($SnO_2$), ITO (Indium Tin Oxide), IZO (Indium Zinc Oxide) IDIXO (Idemitsu Indium X-metal Oxide: Idemitsu Kosan Co., Ltd), or the like, formed into a thickness of 50 to 200 nm, may be used. Alternatively, Al or Au of 100 nm thickness may be used.

Second electrode layer 206 includes a plurality of transparent linear electrodes 206a that transmits readout light and a plurality of opaque linear electrodes 206b that blocks the readout light. Transparent linear electrodes 206a and opaque linear electrodes 206b extend from one end of an image forming area of periodic information imaging radiation image detector 200 to the other end continuously and straightly. As illustrated in FIGS. 30A and 30B, transparent linear electrodes 206a and opaque linear electrodes 206b are disposed alternately in parallel at a predetermined distance.

Transparent linear electrodes 206a are formed of a material that transmits readout light and has conductivity. For example, ITO, IZO, or IDIXO may be used as in first electrode layer 201. The thickness of each electrode 206a is about 100 to 200 nm.

Opaque linear electrodes 206b are formed of a material that blocks the readout light and has conductivity. It is preferable that opaque linear electrodes 206b transmit erasure light, and a combination of one of the transparent conductive materials described above with a color filter is used as the opaque linear electrode 206b. The thickness of the transparent conductive material is about 100 to 200 nm.

As will be described later, an image signal is read out by adjacent transparent linear electrode 206a and opaque linear electrode 206b as a pair. In periodic information imaging radiation image detector 200 of the present embodiment, 20 pairs of transparent linear electrode 206a and opaque linear electrode 206b are disposed in the width of one pixel constituting a radiation image, as illustrated in FIG. 31. That is, 20 linear electrode pairs from first linear electrode pair 211, second linear electrode pair 212, third linear electrode pair 213, and so forth are disposed within the width of one pixel.

As illustrated in FIG. 31, the linear electrode pairs are disposed such that the distance between every other pairs, e.g., the distance between first linear electrode pair 211 and third linear electrode pair 213, or the distance between second linear electrode pair 212 and fourth linear electrode pair 214, corresponds to pitch $P_2$. Pitch $P_2$ is set to a value in the range from 2 to 15 μm. A first linear electrode group is formed of $(2n-1)^{th}$ (n is an integer not smaller than 1 and not greater than 10) linear electrode pair and a second linear electrode group is formed of $(2n)^{th}$ (n is an integer not smaller than 1 and not greater than 10) linear electrode pair.

Then, the first and second linear electrode groups within the width of one pixel described above are alternately disposed in a direction orthogonal to the length direction of the linear electrodes. In this case, the first electrode group and second linear electrode group are disposed so as to be phase shifted by n from each other. Although not shown, transparent linear electrodes 206a of the first linear electrode groups are physically connected to each other with a connection wire, such as a lead wire. Also, transparent linear electrodes 206a of the second linear electrode groups are physically connected to each other with a connection wire, such as a lead wire.

Recording photoconductive layer 202 may be formed of any material as long as it generates charges when exposed to radiation. Here, a-Se based material having excellent properties, such as relatively high quantum efficiency to radiation and high dark resistance, is used. An appropriate layer thickness is in the range from 10 to 1500 Wm. For a mammography application, in particular, a preferable layer thickness is in the range from 150 to 250 μm, and for a general radiography application, a preferable layer thickness is in the range from 500 to 1200 μm.

As for the material of charge transport layer 204, for example, a material having a greater difference in charge mobility between charges charged on first electrode layer 201 when a radiation image is recorded and the charges having opposite polarity (for example, not less than $10^2$, more preferably, not less than $10^3$), is preferably used. In this respect, organic compounds such as polyN-vinylcarbazole (PVK), N,N'-diphenyl-N,N'-bis (3-methylphenyl)-[1,1'-biphenyl]-4,4'-diamine(TPD), discotic liquid crystal, and the like, or semiconductor materials such as TPD-dispersed polymers (polycarbonate, polystyrene, PVK), a-Se doped with 10 to 200 ppm of Cl, $As_2Se_3$, and the like are preferably used. An appropriate thickness of charge transport layer is in the range from 0.2 to 2 μm.

Readout photoconductive layer 205 may be formed of any material as long as it shows conductivity when exposed to readout light. For example, a photoconductive material consisting primarily of at least one of a-Se, Se—Te, Se—As—Te, non-metal phthalocyanine, metal phthalocyanine, MgPc (magnesium phthalocyanine) VoPc (phase II of Vanadyl phthalocyanine, CuPc (cupper phthalocyanine), and the like is preferably used. An appropriate thickness of photoconductive layer 205 is in the range from 5 to 20 μm.

Next, an operation for recording a radiation image to and reading out from the periodic information imaging radiation image detector of the radiation phase image radiographing apparatus according to the third embodiment will be described.

The operation steps from the emission of radiation from radiation emission unit 1 to the formation of self-image by diffraction grating 20 are identical to those of the radiation phase image radiographing apparatus according to the second embodiment, and therefore will not be elaborated upon further here.

Then, as illustrated in FIG. 32A, with a negative voltage being applied to first electrode layer 201 of periodic information imaging radiation image detector 200 by high voltage source 300, radiation representing a self-image formed by Talbot effect of diffraction grating 20 is emitted to periodic information imaging radiation image detector 200 from the side of first electrode layer 201.

The radiation emitted on periodic information imaging radiation image detector 200 transmits through first electrode layer 201 and irradiates recording photoconductive layer 202. Then, recording photoconductive layer 202 generates charge pairs by the irradiation of the radiation, and positive charges of the charge pairs are combined with negative charges charged on the first electrode layer 201 and dissolved, while negative charges of the charge pairs are stored, as latent image charges, in storage section 203 formed at the interface between recording photoconductive layer 202 and charge transport layer 204 (FIG. 32B).

Now, in periodic information imaging radiation image detector 200 of radiation phase image radiographing apparatus of the present embodiment, second electrode layer 206 for collecting charges generated in recording photoconductive layer 202 to storage section 203 is constituted by transparent linear electrode 206a and opaque linear electrode 206b. Therefore, when a voltage is applied to first electrode layer 201 in the manner as described above, electric fields are formed in recording photoconductive layer 202 from transparent linear electrode 206a and opaque linear electrode 206b toward first electrode layer 201 substantially parallel to each other, i.e., substantially perpendicular to the surface of first electrode layer 201. Negative charges generated in recording photoconductive layer 202 are shifted toward each linear electrode along the electric field without spreading and collected in storage section 203, so that transparent linear electrode 206a and opaque linear electrode 206b perform a function equivalent to that of the combination of an amplitude diffraction grating and a detector provided in the later stage of the grating. Accordingly, charges representing image contrast generated by the superimposition of a self-image of the deformed diffraction grating 20 and a virtual diffraction grating formed by the first linear electrode group are stored in a portion of storage section 203 above the first linear electrode group constituted by $(2n-1)^{th}$ (n is an integer not smaller than 1 and not greater than 10) linear electrode pair shown in FIG. 31 and charges representing image contrast generated by the superimposition of a self-image of the deformed diffraction grating 20 and a virtual diffraction grating formed by second linear electrode group are stored a portion of storage section 203 above the second linear electrode group constituted by $2n^{th}$ (n is an integer not smaller than 1 and not greater than 10) linear electrode pair shown in FIG. 31. The image contrast described above generally takes the form of Moire fringes. As described above, the first linear electrode group and second linear electrode group are phase shifted by n from each other, thus signals corresponding to two types of phase components phase shifted from each other by n are recorded in periodic information imaging radiation image detector 200.

Figure 33:
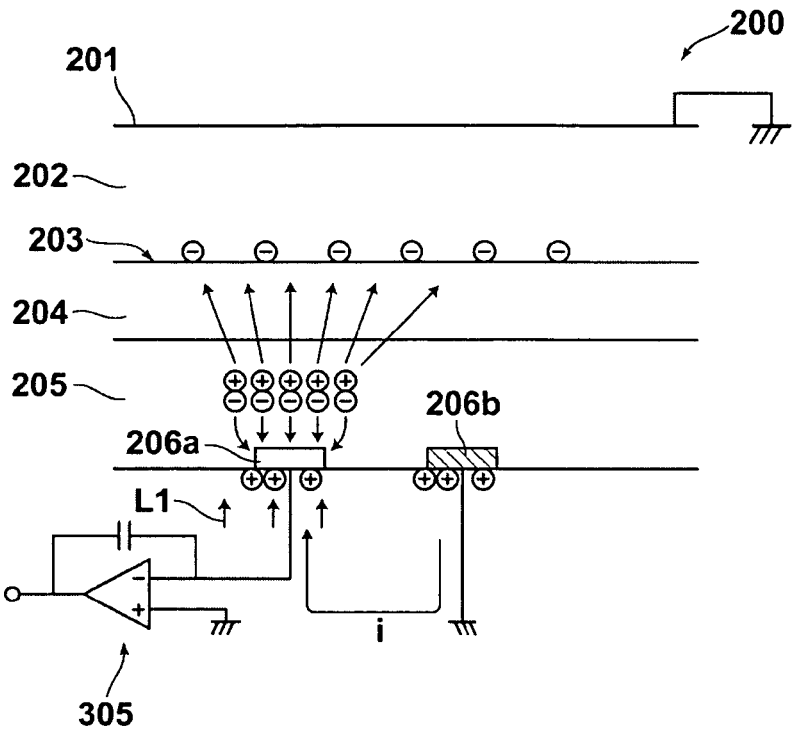
FIG. 33 illustrates a reading operation for reading out a radiation image from the periodic information imaging radiation image detector in the third embodiment of the radiation phase image radiographing apparatus of the present invention.

Then, with the first electrode layer 201 being grounded, readout light L1 is emitted from the side of second linear electrode layer 206, as illustrated in FIG. 33. Readout light L1 transmits through transparent linear electrodes 206a and irradiates readout photoconductive layer 205. Positive charges generated in readout photoconductive layer 205 combine with latent image charges in storage section 203 while negative charges combine with positive charges charged on opaque linear electrode 206b through charge amplifier 305 connected to opaque linear electrode 206b.

A current flows through charge amplifier 305 when the negative charges generated in readout photoconductive layer 205 are combined with the positive charges charged on opaque linear electrode 206b, and the current is integrated and detected as an image signal.

At this time, charges, flowed out from the first linear electrode group of first linear electrode pair 211 and third linear electrode pair 213 shown in FIG. 31, are detected by charge amplifier 305 as an image signal corresponding to a first phase component. In the mean time, charges, flowed out from the second linear electrode group of second linear electrode pair 212 and fourth linear electrode pair 214 shown in FIG. 31, are detected by charge amplifier 305 as an image signal corresponding to a second phase component.

Thereafter, periodic information imaging radiation image detector 200 is shifted by shifting mechanism 55, and the image recording in the detector 40 and image signal reading from the detector 200 are performed at each predetermined position, whereby image signals corresponding to the first and second phase components are detected at each predetermined position.

Image signals detected in the manner as described above are inputted to phase image acquisition unit 6. Then, phase image acquisition unit 6 generates a partial phase image with respect to each detection area of periodic information imaging radiation image detector 200 based on image signals of a plurality of phase components detected by periodic information imaging radiation image detector 200 in each detection area corresponding to the irradiation range of radiation emitted from each radiation source 1a. That is, a partial phase image corresponding to each radiation source 1a is generated. Thereafter, the partial phase images are combined to produce a complete phase image.

For example, in the radiation phase image radiographing apparatus of the third embodiment, image signals corresponding to six types of phase components may be obtained by shifting detector 200 and grating 20 by ⅓ of pitch $P_2$ in a direction orthogonal to the linear electrodes along the respective planes and taking a radiation image at each position.

Also, in the radiation phase image radiographing apparatus of the third embodiment, linear electrode group pairs, in which respective linear electrode groups are disposed in order, may be disposed to different positions so as to have different phases as in the periodic information imaging radiation image detector of second embodiment. This allows image signals corresponding to sufficient number of phase components for forming a phase image to be obtained at the same time without requiring the shifting mechanism.

As described above, it is preferable that each radiation sources 1a emits radiation such that the exposure area at the position of subject 10 is arranged without any space and at an angle that substantially does not influence the diffraction properties of diffraction grating 20 and linear electrode groups of periodic information imaging radiation image detector 200 at peripheral portions of exposure areas at the positions of diffraction grating 20 and periodic information imaging radiation image detector 200. Hereinafter, the angle will be discussed. Here, the allowable range of the angle will be discussed in terms of the positional displacement of linear electrodes of periodic information imaging radiation image detector 200.

Assuming a required pitch of linear electrodes at a position (r, x) away from intersection point Q between central axis C of radiation emitted from radiation source 1a and periodic information imaging radiation image detector 40 by distance x in a direction orthogonal to the linear electrodes to be Δx, Δx can be represented by Formula (13) below (FIG. 24, which is a top view of the radiation phase image radiographing apparatus shown in FIG. 13. The thickness direction in FIG. 24 corresponds to Y direction in FIG. 13.)

$$\Delta x = r\Delta\theta \times \frac{\tan\theta}{\theta} \times \left\{ \sqrt{(r^2 + x^2)} \times \frac{1}{r} \right\} \times \frac{1}{\cos\theta} \qquad (13)$$

where, r is the distance from radiation source 1a (if a slit is used in the radiation emission unit, to be described later, from the position of the slit) to periodic information imaging radiation image detector 40, and rΔθ is the pitch of the linear electrodes at intersection point Q between the central axis C of the radiation beam and periodic information imaging radiation image detector 200.

Here, x/r=tan θ, which is substituted to Formula (13) above, then Δx can be represented by Formula (14) below.

$$\Delta x = r\Delta\theta \times \frac{\tan\theta}{\theta} \times \frac{\sqrt{1+\tan^2\theta}}{\cos\theta} = r\Delta\theta \times \frac{\tan\theta}{\theta\cos^2\theta} \quad (14)$$

Thus, the ratio between the pitch at (r, x) and the pitch rΔθ at intersection point Q can be represented by Formula (15) below.

$$\frac{\Delta x}{r\Delta\theta} = \frac{\tan\theta}{\theta\cos^2\theta} \quad (15)$$

Relationship between θ and Δx/rΔθ obtained based on Formula (15) above is summarized in Table 3 below.

TABLE 3

|  | θ | | | | |
|---|---|---|---|---|---|
|  | 1.0° | 2.0° | 5.0° | 10.0° | 15.0° |
| Δx/rΔθ | 1.0004 | 1.002 | 1.01 | 1.04 | 1.10 |

Here, if Pitch P2 of linear electrode pair is 8 μm and the line width of each linear electrode is 3 μm, the width of one pixel is about 80 μm.

If the phase of each linear electrode pair is shifted about ⅛ of the pitch, it is thought to be undesirable that a signal of different phase component is mixed in the same pixel. Given that the radiation beam spreads from the central axis to X direction (direction orthogonal to the linear electrodes), it is preferable that the positional displacement of linear electrode pair within one pixel is limited to ⅛×½=⅟₁₆=0.5 μm or less.

If the pitch of the linear electrode pair on central axis C is 8 μm, the distance between the centers of linear electrode pairs at each end of a pixel in a peripheral portion of the radiation beam is Δx/rΔθ×8×9.

Accordingly, if Δx/rΔθ×8×9−72<0.5, the condition described above is met.

Thus, Δx/rΔθ<1.007.

Accordingly, it is known from Table 3 above that one-side spread angle θ of the radiation beam in X direction needs to be limited to 2° or less.

For example, if r=1000 mm, 2×1000×tan 2°=70 mm, thus the width of radiation beam emitted from one radiation source 1a in X direction on periodic information imaging radiation image detector 200 needs to be limited to 70 mm or less.

In the radiation phase image radiographing apparatus according to the third embodiment, periodic information imaging radiation image detector 200 to which a negative voltage is applied when recording a radiation image is used. Alternatively, an optical readout type periodic information imaging radiation image detector to which a positive voltage is applied when recording a radiation image may be used.

In the radiation phase image radiographing apparatuses according to the second and third embodiments, the description has been made of a case in which subject 10 is placed between radiation emission unit 1 and diffraction grating 20. When subject 10 is placed between diffraction grating 20 and periodic information imaging radiation image detector 40 or 200, the self-image of diffraction grating 20 produced at the position of periodic information imaging radiation image detector 40 or 200 is deformed by subject 10. Therefore, also in this case, an image signal of a phase component modulated due to subject 10 can be detected by periodic information imaging radiation image detector 40 or 200. That is, in the radiation phase image radiographing apparatus according to the second or third embodiment, subject 10 may be placed between radiation emission unit 1 and diffraction grating 20 or between diffraction grating 20 and periodic information imaging radiation image detector 40 or 200.

Figure 34:
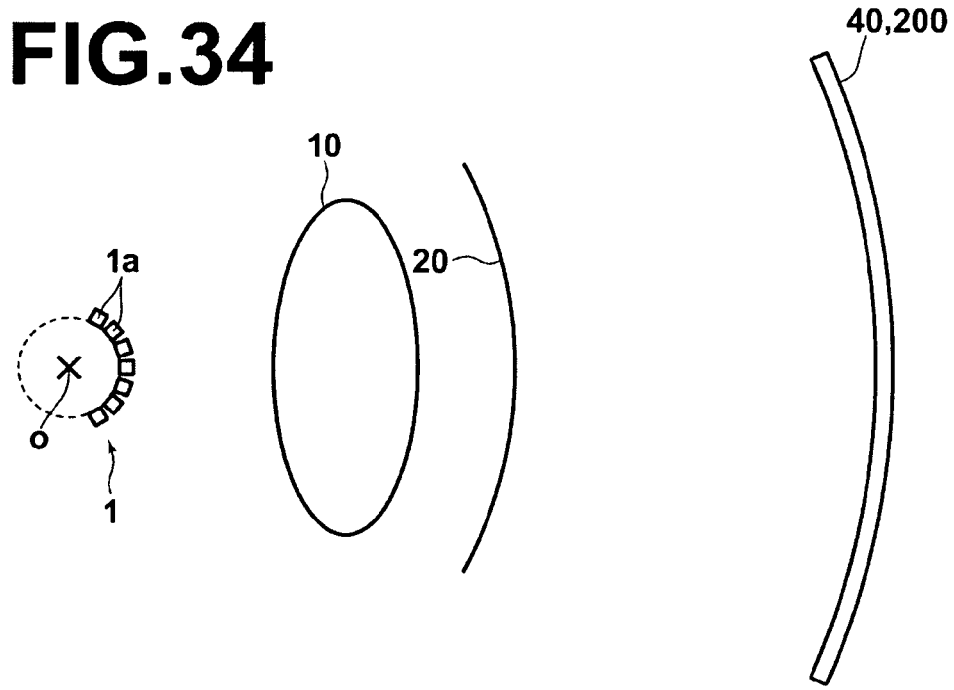
FIG. 34 is a schematic construction diagram of a radiation phase image radiographing apparatus in which radiation sources are disposed along the entire circumference of a cylindrical surface centered on a subject.

Further, in the radiation phase image radiographing apparatuses according to the second and third embodiments, radiation sources 1a are disposed along a planar surface, and diffraction grating 20 and periodic information imaging radiation image detector 40 or 200 are formed along planar surfaces parallel to the planar surface on which multiple radiation sources 1a are disposed. But the structure is not limited to this, and an arrangement may be adopted in which radiation sources 1a are disposed along a cylindrical surface to form radiation emission unit 1, and diffraction grating 20 and periodic information imaging radiation image detector 40 or 200 are formed along cylindrical surfaces concentric with the center O of the cylindrical surface on which multiple radiation sources 1a are disposed, as illustrated in FIG. 34. The arrangement of the radiation sources 1a along a cylindrical surface in the manner as described above may reduce the overall size of radiation emission unit 1 in comparison with the case in which radiation sources 1a are disposed along a planar surface as in the first embodiment, whereby downsizing of the apparatus may be achieved.

In this case, conditions of forming a Talbot interferometer depend on the distance from each radiation source 1a.

When forming periodic information imaging radiation image detector 40 of the second embodiment in the manner as described above, for example, a transparent flexible substrate may be used as substrate 71 of active matrix substrate 70, then unit elements 72 are formed on the flexible substrate, and the flexible substrate may be bonded to a base material having the cylindrical surface described above. Thereafter, semiconductor layer 60 and upper electrode 50 may be formed on active matrix substrate 71. It is also possible to form unit elements 72 on a flexible substrate first, then to form semiconductor layer 60 and upper electrode 50 on the substrate, and finally to bond the flexible substrate to a base material having the cylindrical surface described above, but if semiconductor layer 60 is thick, a crack or peel off is likely to occur. Further, a thin glass substrate reinforced with a plastic film may be used as substrate 71. Where light is emitted from the substrate side, it is preferable to use a transparent substrate and a transparent base material.

When forming periodic information imaging radiation image detector 200 of the third embodiment in the manner as described above, for example, a flexible substrate may be used as substrate 207, then second electrode layer 206 is formed on the flexible substrate, and the flexible substrate may be bonded to a base material having the cylindrical surface described above. Thereafter, readout photoconductive layer 205, charge transport layer 204, recording photoconductive layer 202 and first electrode layer 201 may be formed one after the other on second electrode layer 206. Alternatively, the flexible substrate may be bonded to the base material having the cylindrical surface after forming thereon all of the layers described above.

Further, instead of the flexible substrate, a thin glass substrate reinforced with a plastic film may be used as substrate 207. Where light is emitted from the substrate side, it is preferable to use a transparent substrate and a transparent base material.

Still further, radiation phase image radiographing apparatuses according to the second and third embodiments, and modifications may be applied to X-ray phase CT systems. More specifically, as illustrated in FIG. 35, a rotation mechanism for integrally rotating radiation emission unit 1, diffraction grating 20, and periodic information imaging radiation image detector 40 or 200 in the arrow direction in FIG. 35 with respect to subject 10 placed between radiation emission unit 1 and diffraction grating 20 may be provided, and a three-dimensional image is formed in three-dimensional image forming unit 400 based on a plurality of image data of subject 10 detected by periodic information imaging radiation image detector 40 or 200 according to the rotation by the rotation mechanism.

Figure 35:
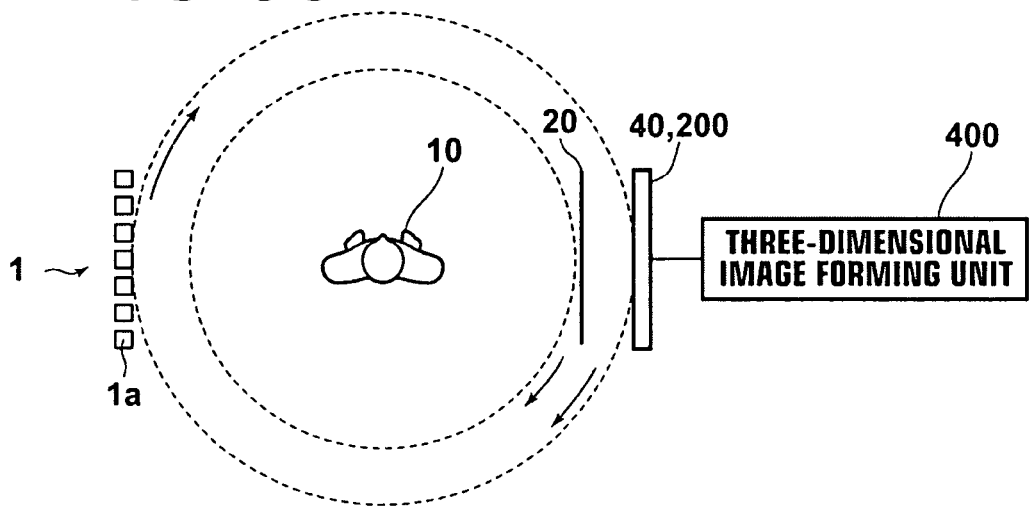
FIG. 35 is a schematic construction diagram of an X-ray phase CT system incorporating the radiation phase image radiographing apparatus according to the second or third embodiment.
Figure 36:
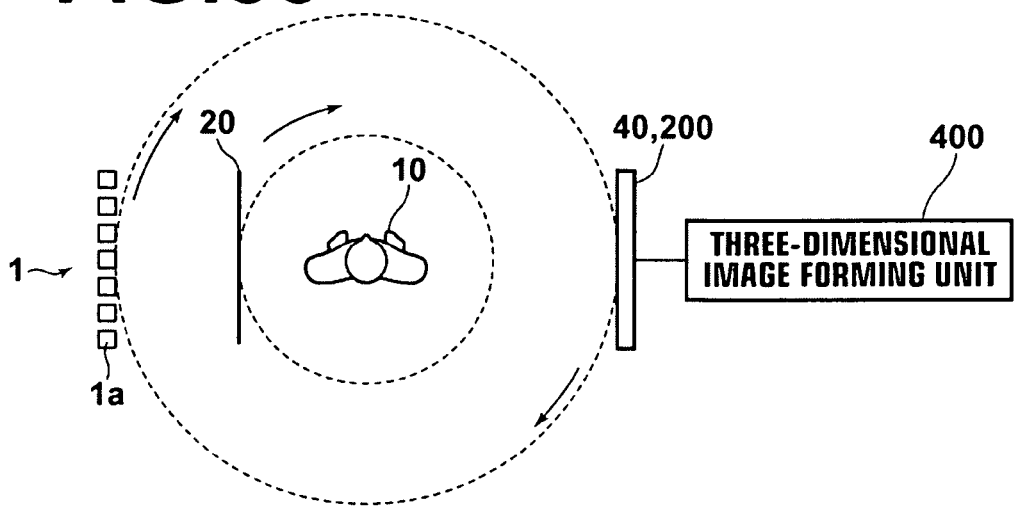
FIG. 36 is a schematic construction diagram of an X-ray phase CT system incorporating the radiation phase image radiographing apparatus according to the second or third embodiment.

Subject 10 may be placed between radiation emission unit 1 and diffraction grating 20, as illustrated in FIG. 35, or between diffraction grating 20 and periodic information imaging radiation image detector 40 or 200, as illustrated in FIG. 36. Note that FIGS. 35 and 36 illustrate only the positional relationships among radiation emission unit 1, diffraction grating 20, periodic information imaging radiation image detector 40 or 200, and subject 10, and do not accurately represent the distance from radiation emission unit 1 to diffraction gratings 20 and the distance from diffraction grating 20 to periodic information imaging radiation image detector 40 or 200. The distance from radiation emission unit 1 to diffraction gratings 20 and the distance from diffraction grating 20 to periodic information imaging radiation image detector 40 or 200 are set so as to satisfy the conditions for obtaining Talbot effect.

The method of forming a three-dimensional image based on a plurality of image data of subject 10 detected by periodic information imaging radiation image detector 40 or 200 is identical to that of a conventional X-ray phase CT system.

In X-ray phase CT systems shown in FIGS. 35 and 36, radiation emission unit 1, diffraction grating 20, and periodic information imaging radiation image detector 40 or 200 are integrally rotated, but radiation emission unit 1 or periodic information imaging radiation image detectors 40 or 200 may be fixedly arranged over the entire circumference along a cylindrical surface centered on the position where subject 10 is placed.

Figure 37:
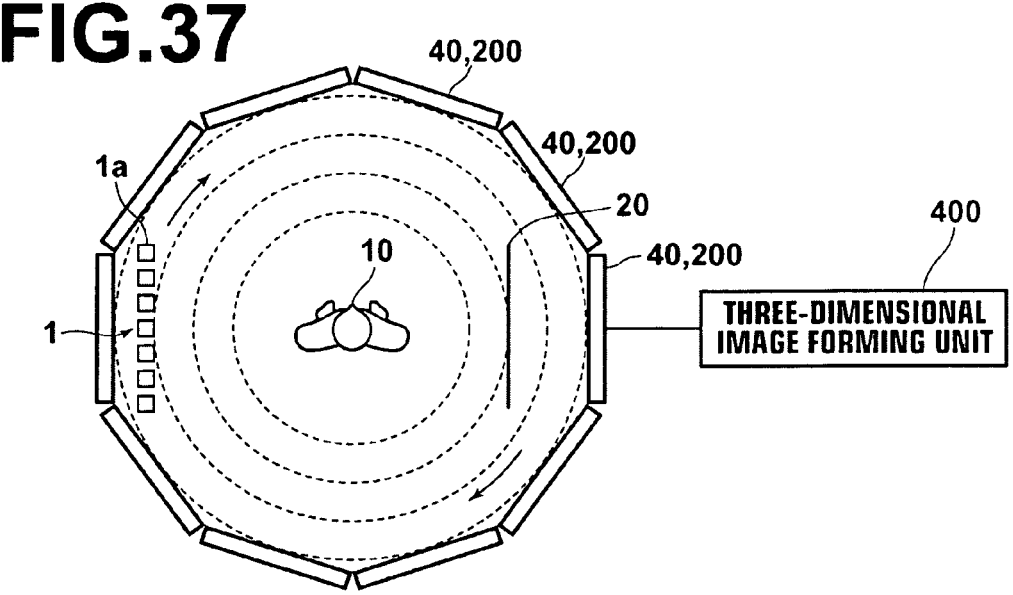
FIG. 37 is a schematic construction diagram of a radiation phase image radiographing apparatus in which radiation image detectors are disposed along the entire circumference of a cylindrical surface centered on a subject.

FIG. 37 shows a configuration in which periodic information imaging radiation image detectors 40 or 200 are disposed over the entire circumference of the cylindrical surface. In the configuration shown in FIG. 37, radiation emission unit 1 and diffraction grating 20 are integrally rotated centered on subject 10.

Figure 38:
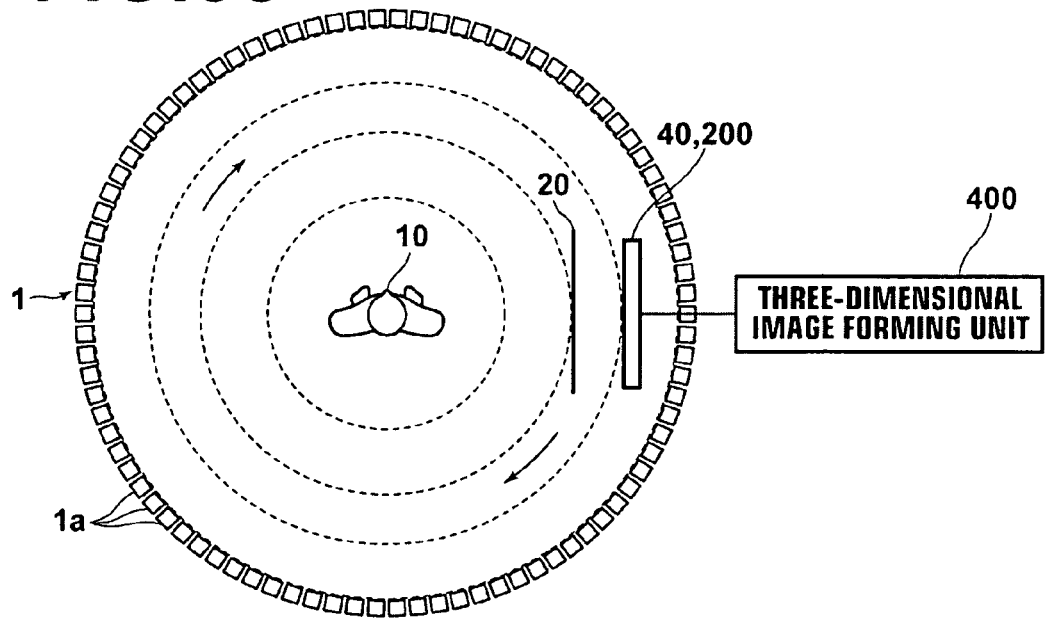
FIG. 38 is a schematic construction diagram of a radiation phase image radiographing apparatus in which radiation sources are disposed along the entire circumference of a cylindrical surface centered on a subject.

FIG. 38 shows a configuration in which each radiation source 1a of radiation emission unit 1 is disposed over the entire circumference of the cylindrical surface. In the configuration shown in FIG. 38, periodic information imaging radiation image detectors 40 or 200 and diffraction grating 20 are integrally rotated centered on subject 10.

Structures of radiation emission unit usable in the radiation phase image radiographing apparatus according to the first embodiment are also usable in the radiation phase image radiographing apparatuses according to the second and third embodiments.

In the radiation phase image radiographing apparatuses according to the second and third embodiments, among image signals detected by each detection area of periodic information imaging radiation image detector 40 or 200, only an image signal detected by an detection area of periodic information imaging radiation image detector 40 or 200 corresponding to an exposure area of radiation emitted from each radiation source 1a and straightly propagated may be extracted, as in the radiation phase image radiographing apparatus of the first embodiment. The detection area corresponding to exposure area of radiation outputted from each radiation source and straightly propagated may be set in advance by emitting radiation from each radiation source 1a without subject 10, and obtaining the exposure area (detection area) on periodic information imaging radiation image detector 40 or 200. Extraction of image signal in the manner as described above allows elimination of scattered radiation influences and improvement in image quality.

In radiation phase image radiographing apparatuses according to the first to third embodiments, if a configuration is adopted in which image signals corresponding to a plurality of phase components are obtained, a phase shift differential image (distribution image of bent angles of radiation caused by refraction effect of a subject) and a phase shift image (integration of phase shift differential) may be calculated using the image signals, which may also be used according to the purpose of the imaging. Calculation methods of a phase shift differential image and a phase shift image are described, for example, in Patent Document 2.

What is claimed is:

1. A radiation phase image radiographing apparatus, comprising:
    a radiation emission unit having multiple radiation sources for emitting radiation onto a subject, the radiation sources being distributed such that radiation emitted from each of the radiation sources and transmitted through the subject forms a part of a projected image of the subject;
    a first diffraction grating configured to be exposed to the radiation emitted from the multiple radiation sources of the radiation emission unit and to produce a Talbot effect by the exposure;
    a second diffraction grating for diffracting the radiation diffracted by the first diffraction grating; and
    a radiation image detector for detecting the radiation diffracted by the second diffraction grating,
    wherein a partial phase image is generated with respect to each detection area of the radiation image detector corresponding to an exposure area of the radiation emitted from each radiation source based on image signals corresponding to a plurality of phase components, each detected by each detection area, and a complete phase image is formed by combining the partial phase images.

2. The radiation phase image radiographing apparatus of claim 1, wherein:
    the multiple radiation sources are disposed along a planar surface; and
    the first and second diffraction gratings are formed respectively along planar surfaces parallel to the planar surface on which the multiple radiation sources are disposed.

3. The radiation phase image radiographing apparatus of claim 1, wherein:
    the multiple radiation sources are disposed along a cylindrical surface; and
    the first and second diffraction gratings are formed respectively along cylindrical surfaces concentric with the cylindrical surface on which the multiple radiation sources are disposed.

4. The radiation phase image radiographing apparatus of claim 1, wherein:
the multiple radiation sources or the radiation image detector is disposed in abutment with a cylindrical surface centered on a position where the subject is placed; and
the first and second diffraction gratings are formed respectively in abutment with cylindrical surfaces concentric with the cylindrical surface to which the multiple radiation sources or the radiation image detector is abutted.

5. The radiation phase image radiographing apparatus of claim 1, wherein each of the multiple radiation sources is a radiation source that emits radiation such that exposure areas of radiation emitted from adjacent radiation sources at a position of the subject overlap with each other without any space between them and at an angle that substantially does not influence diffraction properties of the first and second diffraction gratings in peripheral portions of exposure areas at positions of the first and second diffraction gratings.

6. The radiation phase image radiographing apparatus of claim 1, wherein a spread angle of the radiation emitted from each of the multiple radiation sources in an extending direction of a diffraction member of the first diffraction grating is larger than a spread angle of the radiation in a direction orthogonal to the extending direction.

7. The radiation phase image radiographing apparatus of claim 1, wherein an arrangement area of the multiple radiation sources in an extending direction of a diffraction member of the first diffraction grating is smaller than an arrangement area of the radiation sources in a direction orthogonal to the extending direction.

8. The radiation phase image radiographing apparatus of claim 7, wherein all of the multiple radiation sources are disposed in a line in a direction orthogonal to the extending direction of the diffraction member of the first diffraction grating.

9. The radiation phase image radiographing apparatus of claim 1, wherein each of the radiation sources is a microfocus X-ray source, and a Talbot interferometer is constructed with the first and second diffraction gratings.

10. The radiation phase image radiographing apparatus of claim 1, wherein each of the radiation sources is an X-ray source constituted by an electron source, a metal target, and a slit made of linear members parallel to diffraction members of the first and second diffraction gratings and transmits an X-ray emitted from the metal target, and a Talbot-Lau interferometer is constructed with the first and second diffraction gratings.

11. The radiation phase image radiographing apparatus of claim 1, wherein:
a shifting mechanism for shifting the first and second diffraction gratings in a direction orthogonal to an extending direction of diffraction members of the first and second diffraction gratings is provided; and
a phase image is formed based on image signals detected by the radiation image detector at a plurality of positions according to the shift of the first and second diffraction gratings implemented by the shifting mechanism.

12. The radiation phase image radiographing apparatus of claim 1, wherein, among image signals detected by the radiation image detector, only a signal detected by a detection area of the radiation image detector corresponding to an exposure area of the radiation emitted from each radiation source and propagated straightly is extracted.

13. A radiation phase image radiographing apparatus, comprising:
a radiation emission unit having multiple radiation sources for emitting radiation onto a subject, the radiation sources being distributed such that radiation emitted from each of the radiation sources and transmitted through the subject forms a part of a projected image of the subject;
a diffraction grating configured to be exposed to the radiation emitted from the multiple radiation sources of the radiation emission unit and to produce a Talbot effect by the exposure; and
a periodic information imaging radiation image detector having an electrode structure that substantially functions as an amplitude type diffraction grating, for detecting periodic information of the radiation diffracted by the diffraction grating.

14. The radiation phase image radiographing apparatus of claim 13, wherein:
the multiple radiation sources are disposed along a planar surface, and
the diffraction grating and periodic information imaging radiation image detector are formed respectively along planar surfaces parallel to the planar surface on which the multiple radiation sources are disposed.

15. The radiation phase image radiographing apparatus of claim 13, wherein:
the multiple radiation sources are disposed along a cylindrical surface; and
the diffraction grating and periodic information imaging radiation image detector are formed respectively along cylindrical surfaces concentric with the cylindrical surface on which the multiple radiation sources are disposed.

16. The radiation phase image radiographing apparatus of claim 13, wherein:
the multiple radiation sources or the periodic information imaging radiation image detector is disposed in abutment with a cylindrical surface centered on a position where the subject is placed; and
the diffraction grating is formed in abutment with a cylindrical surface concentric with the cylindrical surface to which the multiple radiation sources or the periodic information imaging radiation image detector is abutted.

17. The radiation phase image radiographing apparatus of claim 13, wherein each of the multiple radiation sources is a radiation source that emits radiation such that exposure areas of radiation emitted from adjacent radiation sources at a position of the subject overlap with each other without any space between them and at an angle that substantially does not influence diffraction properties of the diffraction grating and periodic information imaging radiation image detector in peripheral portions of exposure areas at positions of the diffraction grating and periodic information imaging radiation image detector.

18. The radiation phase image radiographing apparatus of claim 13, wherein a spread angle of the radiation emitted from each of the multiple radiation sources in an extending direction of a diffraction member of the diffraction grating is larger than a spread angle of the radiation in a direction orthogonal to the extending direction.

19. The radiation phase image radiographing apparatus of claim 13, wherein an arrangement area of the multiple radiation sources in an extending direction of a diffraction member of the diffraction grating is smaller than an arrangement area of the radiation sources in a direction orthogonal to the extending direction.

20. The radiation phase image radiographing apparatus of claim 19, wherein all of the multiple radiation sources are disposed in a line in a direction orthogonal to the extending direction of the diffraction member of the diffraction grating.

21. The radiation phase image radiographing apparatus of claim 13, wherein each of the radiation sources is a microfocus X-ray source, and a Talbot interferometer is constructed with the diffraction grating and periodic information imaging radiation image detector.

22. The radiation phase image radiographing apparatus of claim 13, wherein each of the radiation sources is an X-ray source constituted by an electron source, a metal target, and a slit made of linear members parallel to a diffraction member of the diffraction grating and transmits an X-ray emitted from the metal target, and a Talbot-Lau interferometer is constructed with the diffraction grating and periodic information imaging radiation image detector.

23. The radiation phase image radiographing apparatus of claim 13, wherein a phase image is formed based on image signals corresponding to a plurality of phase components detected by the periodic information imaging radiation image detector without shifting the diffraction grating and periodic information imaging radiation image detector in a direction orthogonal to the extending direction of a diffraction member of the diffraction grating.

24. The radiation phase image radiographing apparatus of claim 13, wherein a partial phase image is generated with respect to each detection area of the periodic information imaging radiation image detector corresponding to an exposure area of the radiation emitted from each radiation source based on image signals corresponding to a plurality of phase components, each detected by each detection area, and a complete phase image is formed by combining the partial phase images.

25. The radiation phase image radiographing apparatus of claim 13, wherein, among image signals detected by the periodic information imaging radiation image detector, only a signal detected by a detection area of the periodic information imaging radiation image detector corresponding to an exposure area of the radiation emitted from each radiation source and propagated straightly is extracted.

* * * * *